US012551405B2

(12) United States Patent
Drach et al.

(10) Patent No.: US 12,551,405 B2
(45) Date of Patent: Feb. 17, 2026

(54) PRESSURIZED GAS POWERED LIQUID TRANSFER DEVICE AND SYSTEM

(71) Applicant: Enable Injections, Inc., Cincinnati, OH (US)

(72) Inventors: Greg Drach, Liberty Township, OH (US); James Lowe, Clarksville, OH (US); Caitlin Knobbe, Burlington, KY (US); Daniel Geiger, Newport, KY (US); David Stefanchik, Morrow, OH (US)

(73) Assignee: Enable Injections, Inc., Cincinnati, OH (US)

( * ) Notice: Subject to any disclaimer, the term of this patent is extended or adjusted under 35 U.S.C. 154(b) by 344 days.

(21) Appl. No.: 18/040,486

(22) PCT Filed: Aug. 4, 2021

(86) PCT No.: PCT/US2021/044451
§ 371 (c)(1),
(2) Date: Feb. 3, 2023

(87) PCT Pub. No.: WO2022/031784
PCT Pub. Date: Feb. 10, 2022

(65) Prior Publication Data

US 2023/0285243 A1 Sep. 14, 2023

Related U.S. Application Data

(60) Provisional application No. 63/060,924, filed on Aug. 4, 2020.

(51) Int. Cl.
*A61J 1/20* (2006.01)
*A61M 5/178* (2006.01)

(52) U.S. Cl.
CPC ........... *A61J 1/2075* (2015.05); *A61J 1/2082* (2015.05); *A61J 1/2089* (2013.01); *A61M 5/1782* (2013.01)

(58) Field of Classification Search
CPC .............. A61M 5/2053; A61M 5/1782; A61M 5/2046; A61J 1/201; A61J 1/2082; A61J 1/2096; A61J 1/2089; A61J 1/2075
See application file for complete search history.

(56) References Cited

U.S. PATENT DOCUMENTS 5,662,642 A * 9/1997 Isono .................... A61J 1/2089 604/408
2008/0051718 A1 2/2008 Kavazov et al.
(Continued)

FOREIGN PATENT DOCUMENTS

JP H 8-38532 A 2/1996
JP 2014012214 A 1/2014
(Continued)

OTHER PUBLICATIONS

European Search Report and Written Opinion, counterpart EP App. No. 21854657.0-1122 / PCT/US2021/044451 (Jul. 24, 2024) (7 pages).
(Continued)

*Primary Examiner* — Ariana Zimbouski
(74) *Attorney, Agent, or Firm* — Cook Alex Ltd.

(57) ABSTRACT

A transfer device for transferring a medical fluid from a vial to a medical fluid injection device includes a vial holder where a vial spike positioned within the vial holder is configured to enter a vial containing a medical fluid when the vial is inserted into the vial holder. An expansion chamber having an interior cavity is in fluid communication with the vial spike. A pressurized gas cartridge is positioned with the interior cavity of the expansion chamber, while a puncture tip is configured to puncture the pressurized gas
(Continued)

cartridge when actuated by a user. The vial spike is also configured to be in fluid communication with an injection device attached to the transfer device.

15 Claims, 22 Drawing Sheets

(56) References Cited

U.S. PATENT DOCUMENTS

| | | | | |
|---|---|---|---|---|
| 2011/0186177 | A1* | 8/2011 | Lanier, Jr. ......... | A61M 5/14248 141/383 |
| 2011/0220116 | A1 | 9/2011 | Lowenstein et al. | |
| 2016/0144105 | A1* | 5/2016 | Hooven .................. | A61M 5/20 604/132 |
| 2018/0110922 | A1* | 4/2018 | Dunki-Jacobs ....... | A61J 1/2075 |
| 2020/0061292 | A1 | 2/2020 | Dunki-Jacobs et al. | |

FOREIGN PATENT DOCUMENTS

| | | | |
|---|---|---|---|
| KR | 1020100122916 | A | 11/2010 |
| WO | WO2016/154413 | A1 | 9/2016 |
| WO | WO2019/079335 | A1 | 4/2019 |
| WO | WO2021/016567 | A1 | 1/2021 |

OTHER PUBLICATIONS

Notice of Reasons for Refusal and English-language machine translation, counterpart Japanese App. No. 2022-148009 (Jun. 6, 2023) (8 pages).

International Search Report and Written Opinion, counterpart International Appl. No. PCT/US2021/044451, (Nov. 22, 2021) (11 pages).

* cited by examiner

PRESSURIZED GAS POWERED LIQUID TRANSFER DEVICE AND SYSTEM

CLAIM OF PRIORITY

This application is the U.S. National Stage of PCT International Patent Application No. PCT/US2021/044451, filed Aug. 4, 2021, which claims priority to and the benefit of U.S. Provisional Patent Application No. 63/060,924, filed Aug. 4, 2020, the contents of which are hereby incorporated by reference in their entirety.

FIELD OF THE INVENTION

The present subject matter relates generally to devices for transferring a fluid from a vial to a medical device and, in particular, to a pressurized gas powered device and system for transferring liquid medication from a source vial to an injection device and/or for mixing, diluting or reconstituting a medication and transferring the resulting liquid medication into an injection device.

BACKGROUND

Injection devices that are worn by a patient temporarily or for extended periods are well known in the medical field. The subject matter of this application relates to a transfer device for use particularly but not exclusively with the injection device described in commonly assigned PCT Published Application No. WO 2014/204894, published Dec. 24, 2014, and which is hereby incorporated by reference in its entirety. That injection device includes an internal resilient bladder that may be filled with any suitable injectable medicament, whether drug, antibiotic, biologic or other injectable, for subcutaneous injection, typically a bolus injection, into a patient while the device is being worn by the patient.

This injection device must be filled (wholly or partially) with the desired injectable before injection into the patient. The above PCT published application also discloses a variety of transfer devices for transferring an injectable into the injection device from a source such as a vial or vials. In some situations, the injectable must be diluted or reconstituted, and various devices are disclosed in the above application for accomplishing that. The present application discloses additional novel designs and improvements, allowing lower cost of manufacture and less waste to dispose, for such transfer devices for transferring, diluting and/or reconstituting. The transfer devices described herein may be variously referred to as transfer module, accessories, add-ons or by other suitable terminology, without intending any limitation on the structure or function of the device not set forth herein.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a transfer device for transferring a medical fluid from a vial to a medical fluid injection device includes a vial elevator configured to receive a vial containing a medical fluid and a vial elevator shaft within which the vial elevator moves between an extended position and a retracted position. A vial spike is positioned within the vial elevator shaft so that the vial spike is positioned within the vial when the vial elevator is in the retracted position. An expansion chamber in fluid communication with the vial spike via a gas passage. An injection device port is in fluid communication with the vial spike via a liquid passage. A pressurized gas cartridge is positioned with the expansion chamber. The transfer device also includes a puncture tip. A trigger spring has a hammer. The trigger spring is configured to be deflected and released as the vial elevator moves from the extended position into the retracted position. A flexible wall portion is positioned adjacent to the pressurized gas cartridge or the puncture tip and configured to be engaged by the hammer of the trigger spring upon release of the trigger spring after deflection so that the flexible wall portion causes the puncture tip to puncture the pressurized gas cartridge so as to pressurize the expansion chamber.

In another aspect, a method of transferring a liquid medication from a vial to an injection device includes the steps of: puncturing a pressure canister using a puncture tip by providing relative movement between the pressure canister and the puncture tip using a trigger spring that is deflected and then released; depressurizing air from the punctured pressure canister in an expansion chamber; directing air from the expansion chamber to the vial so as to force liquid medication out of the vial and directing the liquid mediation from the vial to the injection device.

DESCRIPTION

Figure 1:
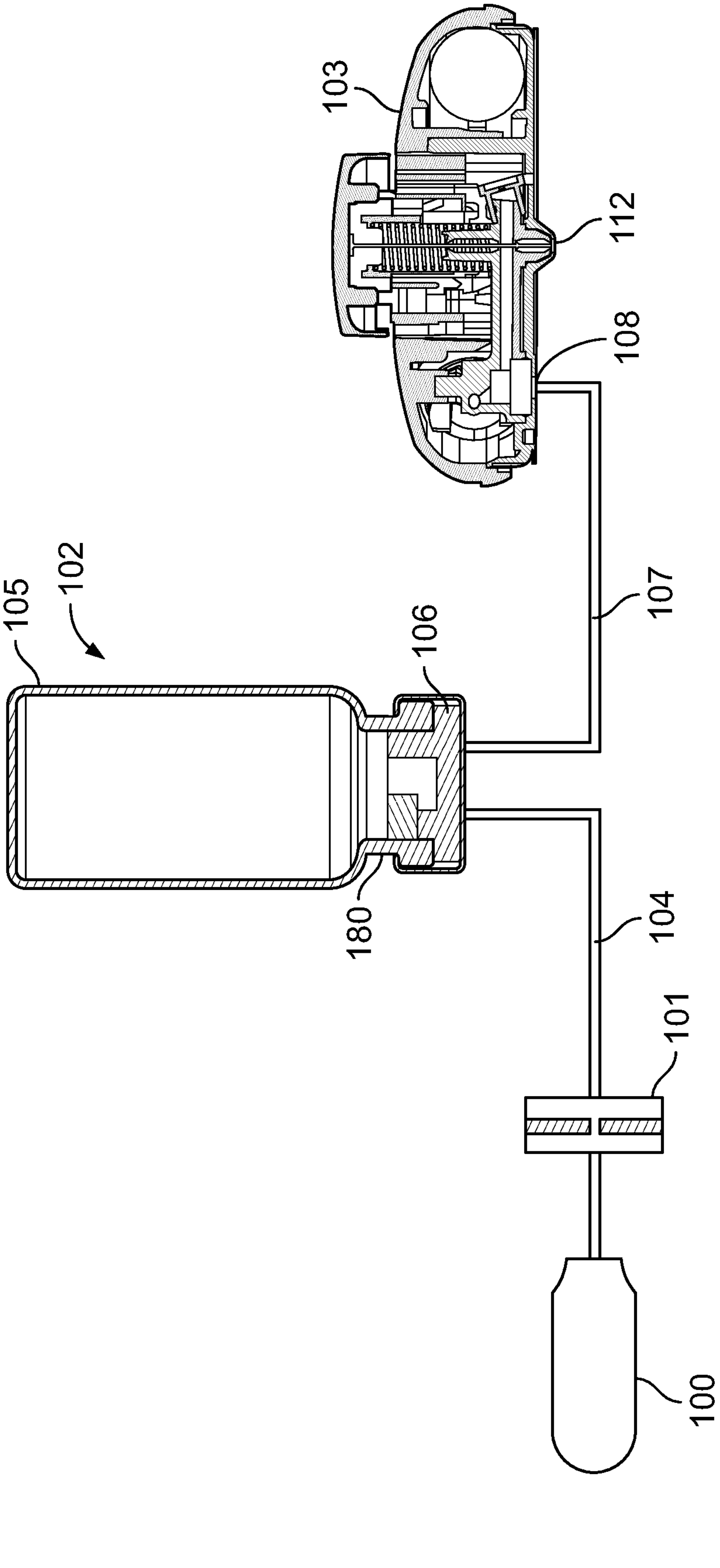
FIG. 1 is a schematic view of a single vial pressurized gas powered transfer system and an injection device.

As described in commonly assigned prior published PCT International Application Publication No. WO 2016/154413, published on Apr. 25, 2019, which is hereby incorporated by reference herein in its entirety, FIG. 1 is a diagrammatic view of a single vial transfer system, including a pressure vessel in the form of a prefilled pressurized gas cylinder or cartridge 100, a flow restrictor and/or pressure regulator 101, a liquid medicament vial 102 and an injection device 103. The gas cylinder may be any suitable cylinder commercially available or may be a custom cylinder. For example, a variety of potential cylinders are available with high pressure gas filled disposable cylinders in capacities from 1 to 1000 cc. The cylinders may be charged to suitable pressures up to 2000-3000 psig or more. It is to be understood that relatively small capacity disposable cylinders will be suitable for the present subject matter. For example, the cylinder may have a volume of 10 ml or less, and more preferably less than 5 ml, such as 1-2 ml, pressurized to 500 psig or more, such as from 900 psig up to 2000-3000 psig or more.

The gas may be any suitable gas, such as, but not exclusively, an inert gas. As it will come in contact with medicament, the gas is preferably pathogen free—i.e., free of active pathogens. Nitrogen or argon may be suitable gases. When released from the cylinder, such as by puncture by a piercing pin, the gas is directed through a suitable flow path from the cylinder through the flow restrictor and/or pressure regulator 101 to the vial 102. Alternatively, the gas that exits the cylinder could be directed through a filter with pore size of 0.2 μm or less to filter the gas.

The flow restrictor and/or pressure regulator 101 may be of any suitable configuration. As an example only, in an embodiment of the disclosure described below, the flow restrictor and pressure regulator may take the form of a chamber formed in a device within which the cartridge is positioned and to which the vial 102 and injection device 103 are attached. From the restrictor/regulator, flow path 104 conducts the gas to the vial 102. The restrictor/regulator could take the form of a filter described above.

The vial 102 may be a standard drug vial with a rigid container portion 105 usually glass, open at one end and sealed by a piercable diaphragm or septum 106 of latex, silicone or other material. The present process is preferably carried out with the vial in an inverted vertical position so that the gas flows to the closed end of the vial, forcing essentially all the medicament from the vial under the force of the pressurized gas.

From the vial, flow path 107 directs the medicament under the pressure of the gas to a suitable vessel such as an injection device 103, an example of which is described in commonly assigned prior published PCT International Application Publication No. WO 2014/204894, noted previously. The injection device may have a liquid reservoir, such as an expandable reservoir for receiving the medicament, for example a reservoir that expands under pressure from the medicament. The reservoir may be biased to expel the medicament upon user actuation of the injection device once removed from the flow path 107. As an example only, the injector capacity can be 1-50 mL.

It should be noted that "injectable fluid," "injectable," "drug," "medicament" and like terms are used interchangeably herein.

The undersurface of the injection device 103 may include a filling port 108 and a dispense port 112. As illustrated in FIG. 1, the filling port 108 is the interface that allows the transfer apparatus filling path 107 to transfer liquid to the injection device 103. The filling port 108 preferably includes a check valve to prevent pressurized injectable from leaking out of the injection device 103 when the injection device is removed from the transfer apparatus and the filling port 108 is removed from the filling path 107.

The medicament is expelled from the injection device 103 via an injection cannula that passes through the dispense port 112.

Figure 2:
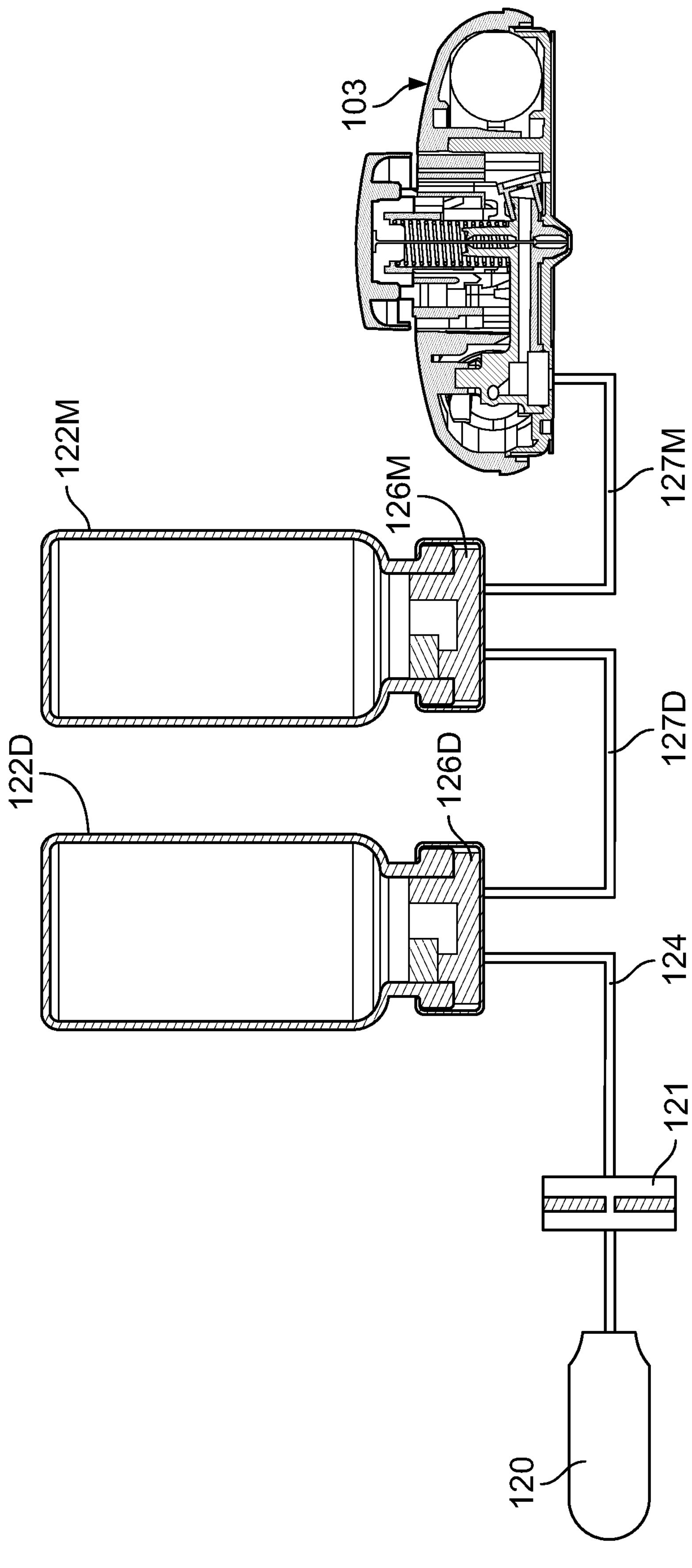
FIG. 2 is a schematic view of a dual vial pressurized gas powered transfer system and an injection device.

For purposes of illustration and not limitation, FIG. 2 is a diagrammatic view of a pressurized gas powered dual vial re-suspension and transfer system, including a pressure vessel in the form of a prefilled pressurized gas cylinder or cartridge 120, a flow restrictor and/or pressure regulator 121, a liquid diluent vial 122D, a medicament vial 122M and the injection device 103 of FIG. 1. (Each vial 122D and 122M could also contain liquid medicament). As in FIG. 1, the gas cylinder 120 may be any suitable cylinder commercially available or may be a custom cylinder.

Also similar to the single vial system, the gas may be any suitable gas, such as, but not exclusively, an inert gas preferably pathogen free—i.e., free of active pathogens. When released, such as by puncture by a piercing pin, the gas is directed through a suitable flowpath from the cylinder through the flow restrictor and/or pressure regulator 121 into the diluent vial 122D. Alternatively, the gas that exits the cylinder could be directed through a filter with pore size of 0.2 μm or less to filter the gas.

As in the system of FIG. 1, the flow restrictor and/or pressure regulator 121 may be of any suitable configuration, including a chamber formed in a device within which the cartridge is positioned and to which the vials 122D and 122M and injection device 103 are attached. From the restrictor/regulator, flow path 124 conducts the gas to the vial 122D. The restrictor/regulator could take the form of a filter described above.

The diluent (or first liquid medicament) vial 122D and medicament (or second liquid medicament) vial 122M may each be of standard drug vial configuration with a rigid container portion usually glass, open at one end and sealed by a piercable diaphragm or septum 126D and 126M of latex, silicone or other material. The present process is preferably carried out with the vials in inverted vertical position so that the gas flows to the closed end of the vials, forcing essentially all the diluent and/or medicament from the vials under the force of the pressurized gas, before any gas exits the medicament vial.

From the diluent (or first liquid medicament) vial 122D, flow path 127D directs the diluent (or liquid medicament) under the pressure of the gas into the medicament vial 122M, where it may re-suspend the medicament if in a dry of lyophilized form or dilute the medicament if in liquid concentrated form (or simply combine or mix with the medicament if in liquid non-concentrated form). From the medicament vial 122M, combined medicament and diluent or diluted or mixed liquid medicament flows through flow path 127M under the pressure of the gas to any suitable vessel, such as an injection device 103 as disclosed in the previously identified PCT application.

Figure 3:
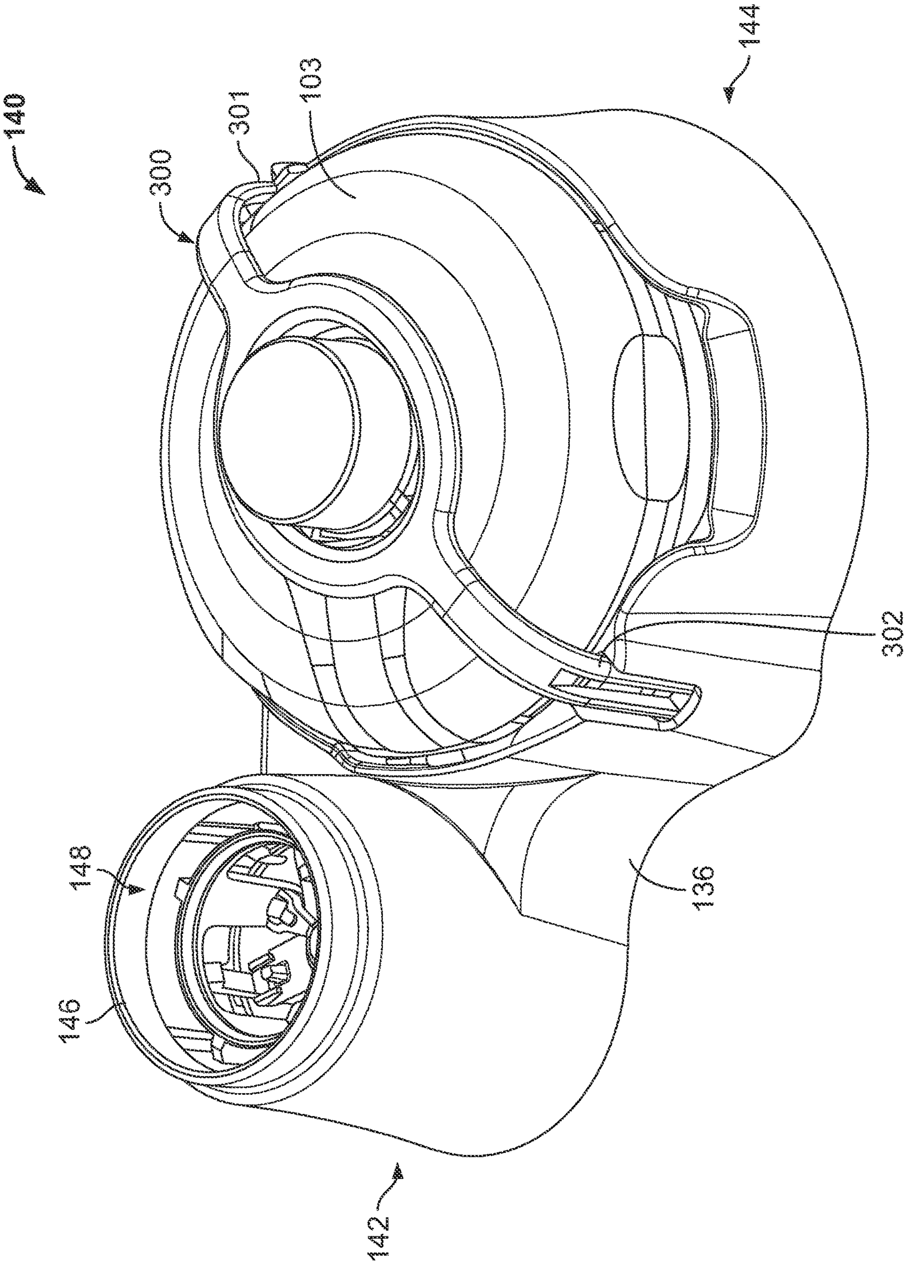
FIG. 3 is perspective view of an embodiment of the pressurized gas powered transfer device of the disclosure with an injection device attached.
Figure 4:
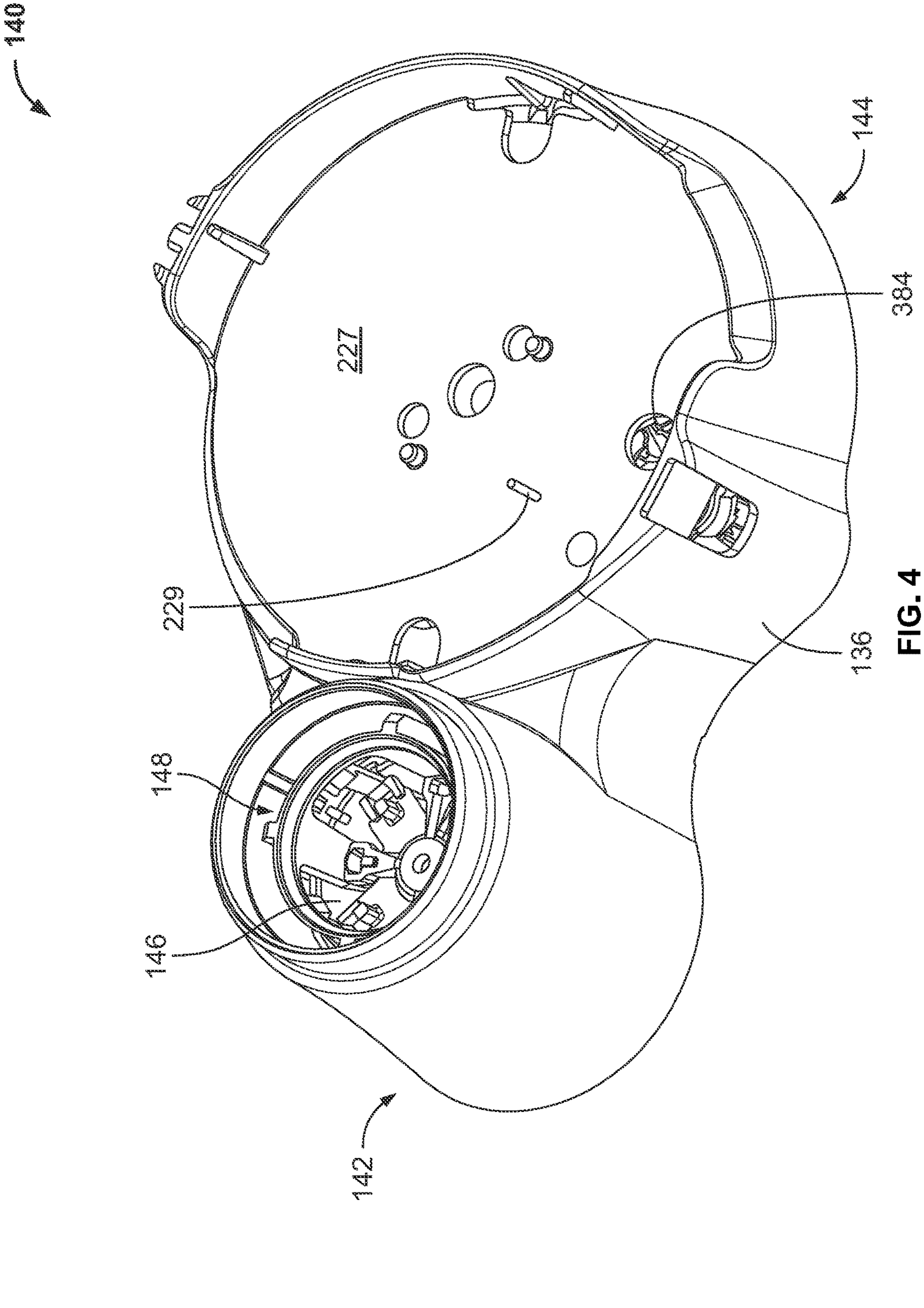
FIG. 4 is a perspective view of the pressurized gas powered transfer device of FIG. 3 with the injection device removed.
Figure 5A:
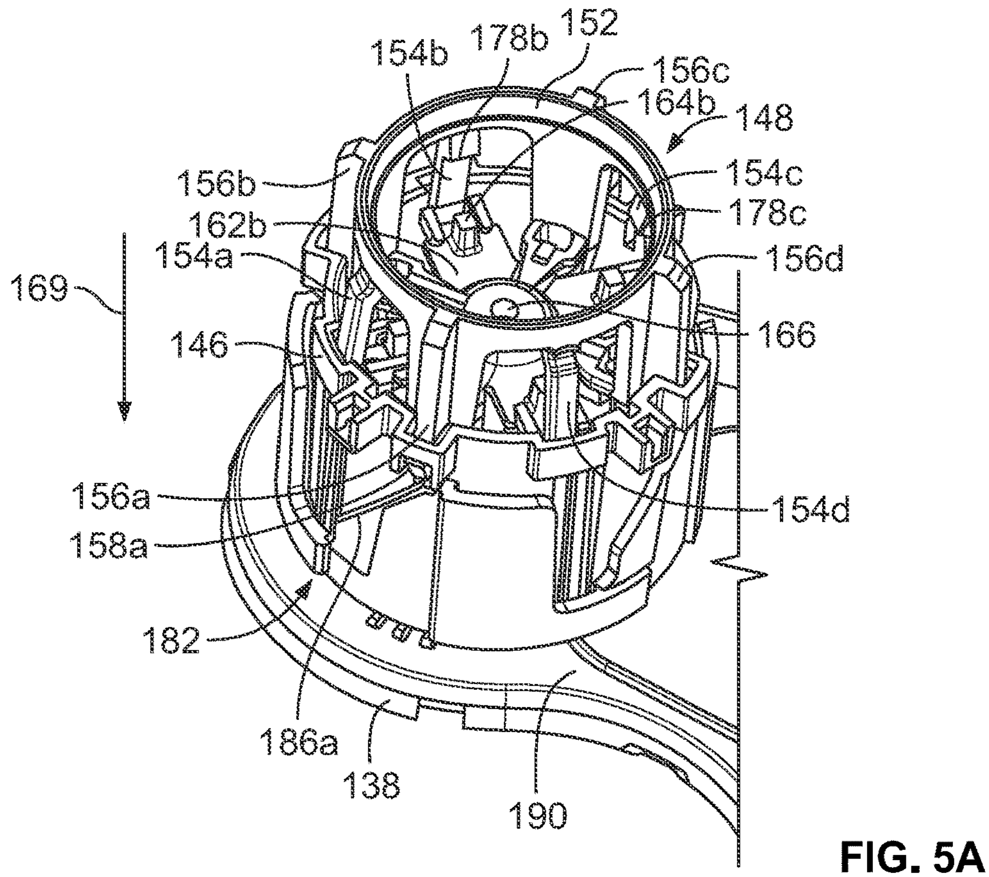
FIG. 5A is an enlarged perspective view of the vial holder of the transfer device of FIGS. 3 and 4 with the housing cover removed.
Figure 5B:
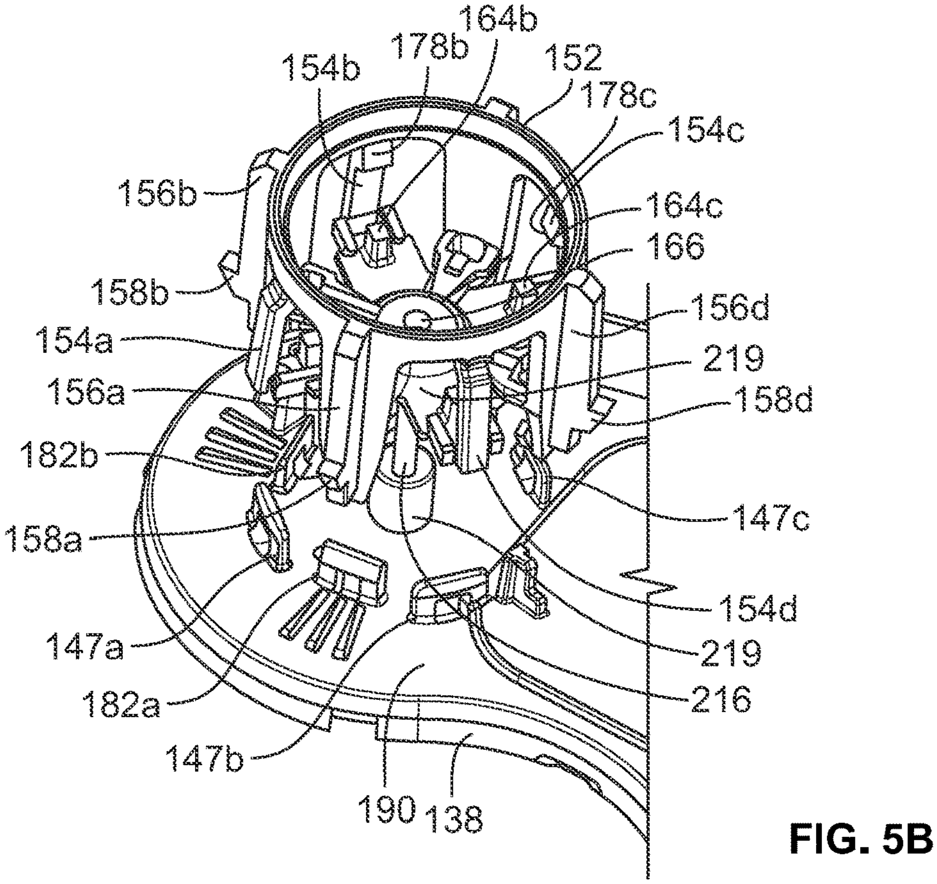
FIG. 5B shows the vial holder of FIG. 5A with the cam ring and elevator shaft removed.
Figure 6A:
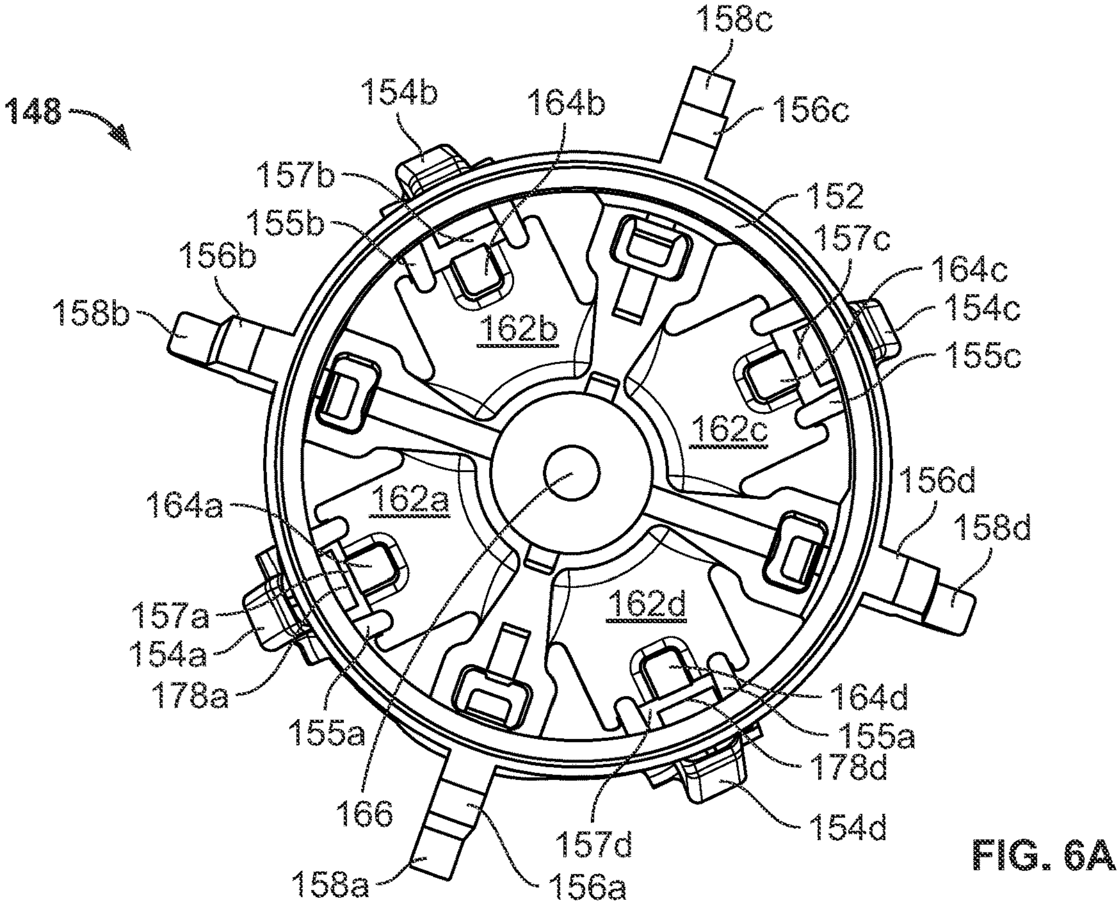
FIG. 6A is an enlarged top plan view of the vial elevator of FIGS. 5A and 5B.
Figure 6B:
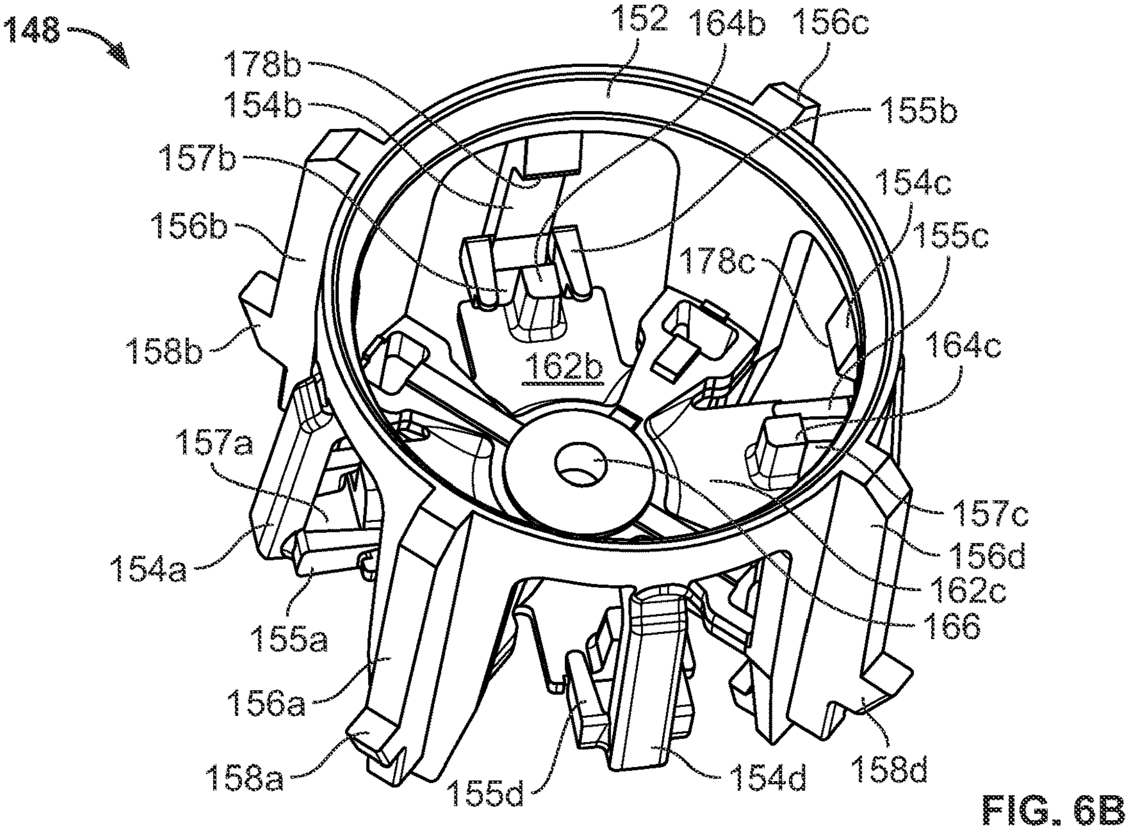
FIG. 6B is a perspective view of the vial elevator of FIG. 6A.
Figure 10A:
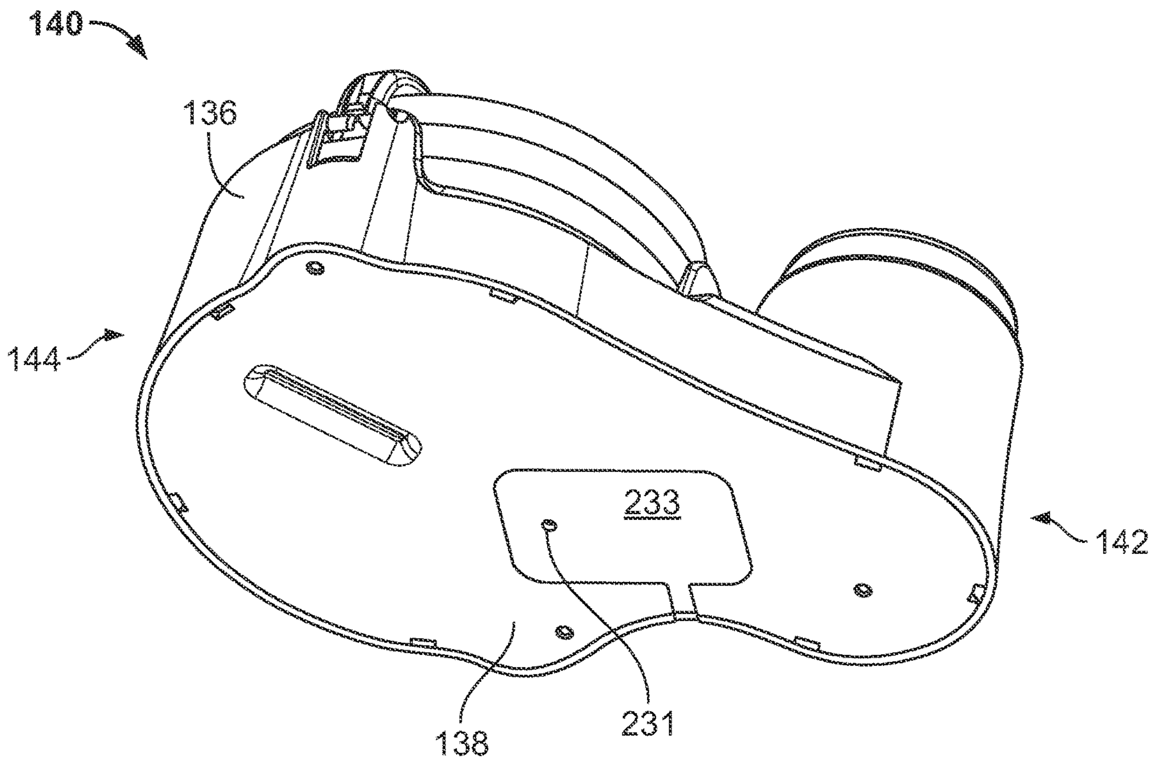
FIG. 10A is a bottom perspective view of the transfer device of FIG. 3.

An embodiment of the pressurized gas powered transfer device of the disclosure is indicated in general at 140 in FIGS. 3 and 4. The transfer device includes a housing cover 136 and a baseplate 138 (FIGS. 5A, 5B and 10A). The transfer device includes two main portions: (1) a vial holder portion, indicated in general at 142, and (2) a gas expansion portion, indicated in general at 144. As illustrated in FIG. 3 and explained in greater detail below, an injection device 103 may be docked to the gas expansion portion 144 to receive a liquid medicament.

While the embodiments disclosed below use a single vial, alternative embodiments include transfer stations that may accommodate two or more vials in the manner illustrated in FIG. 2.

In addition, while embodiments of the transfer device discussed below are single use, disposable devices, alternative embodiments include reusable transfer devices.

The vial holder 142 includes a vial elevator shaft, indicated at 146 in FIGS. 3 and 4 within which is received a vial elevator, indicated in general at 148. As is described and illustrated in commonly assigned PCT International Application Publication No. WO 2019/079335, the contents of which are hereby incorporated by reference, the vial elevator 148 vertically slides within the vial elevator shaft 146 in a telescoping fashion between a raised or extended position, wherein the vial elevator 148 is in the position illustrated in FIGS. 3-5B and 9, and a lowered or retracted position, wherein the vial elevator 148 is positioned down within the vial elevator shaft 146.

As illustrated in FIGS. 5A and 5B, wherein the housing cover has been removed, the vial elevator shaft 146 is secured to a passage plate 190 of the transfer device in a fixed fashion. More specifically, the bottom portion of the vial elevator shaft 146 includes hooks (one of which is illustrated at 139 in FIG. 7) that engage rectangular loop structures 147*a*-147*c* (FIG. 5B) of the passage plate 190 in a snap fit connection.

As illustrated in FIGS. 5A, 5B and 6A, 6B, the vial elevator 148 includes a circular rim 152 from which lock arms 154*a*-154*d* downwardly extend. The distal end of each lock arm 154*a*-154*d* is bifurcated so that each features a claw 155*a*-155*d* defining a notch 157*a*-157*d*. In addition, the upper portion of each lock arm 154*a*-154*d* includes a vial locking shoulder 178*a*-178*d*.

In addition, as further illustrated in FIGS. 5A, 5B and 6A, 6B, splines 156*a*-156*d* extend down from the rim 152 with each including an outward facing camming hook 158*a*-158*d*. Stop tabs 162*a*-162*d* radially extend from a central bottom portion of the elevator, and each features a stop pin 164*a*-164*d*. The distal ends of the stop tabs 162*a*-162*d* engage the distal tips of claws 155*a*-155*d* so that inward movement of the claws is blocked.

An opening 166 (FIGS. 6A and 6B) is formed in the center of the bottom of the vial elevator 148 and receives an upwardly pointing vial spike mounted to the passage plate 190 (FIGS. 5A and 5B), as will be explained in greater detail below.

Figure 7:
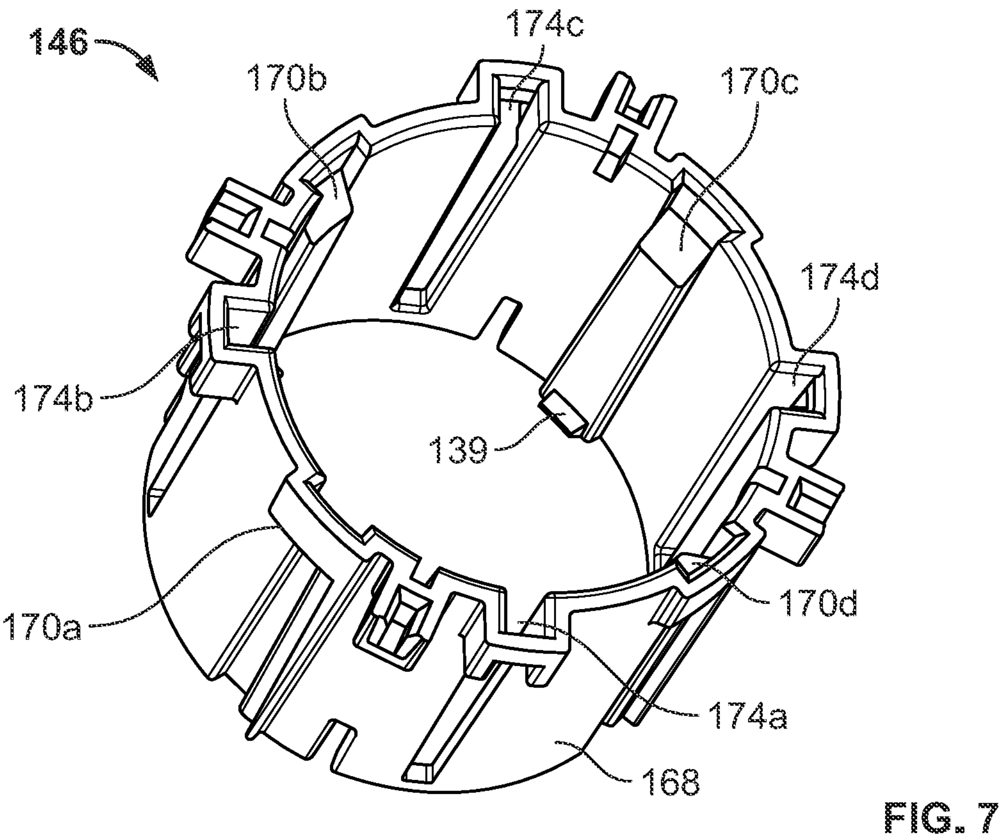
FIG. 7 is an enlarged perspective view of the elevator shaft of FIG. 5A.

As illustrated in FIG. 7, where the vial elevator shaft is individually illustrated and indicated in general at 146, the vial elevator shaft has a sidewall 168 that includes inwardly facing channels 174*a*-174*d* that receive the splines 156*a* and 156*b* of the vial elevator 148 in a sliding fashion to provide radial alignment of the vial elevator in the vial elevator shaft and to provide a smooth transition as the vial elevator moves.

As also illustrated in FIG. 7, the inner surface of sidewall 168 includes inwardly extending cam ramps 170*a*-170*d*.

Figure 8:
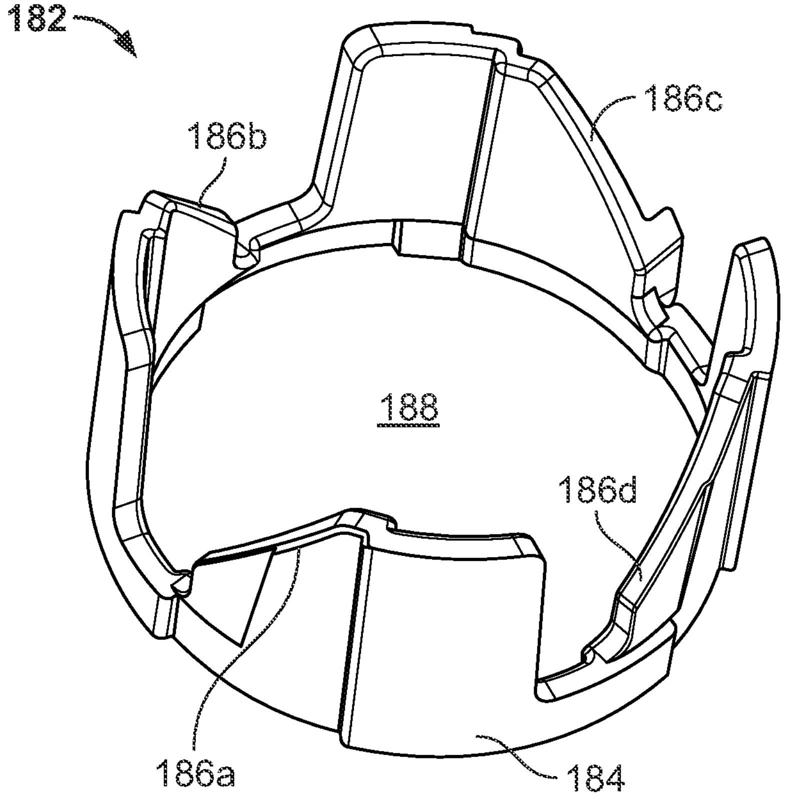
FIG. 8 is an enlarged perspective view of the cam ring of FIG. 5A.

A cam ring, indicated in general at 182 in FIGS. 5A and 8, includes a sidewall 184 having notches and a central opening 188. Each notch includes an edge so that camming surfaces 186*a*-186*d* are defined.

As illustrated in FIG. 5A, the central opening of the cam ring 182 is sized to receive the vial elevator shaft 146 so that the cam ring is rotatably positioned upon the passage plate 190. As illustrated in FIG. 5A, when the vial elevator is in the raised or extended position, the hook 158*a* of spline 156*a* is positioned at the top of the camming surface 186*a* of the cam ring 182. The hooks 158*b*-158*d* of splines 156*b*-156*d* are in the same position with respect to camming surfaces 186*b*-186*d*.

Figure 9:
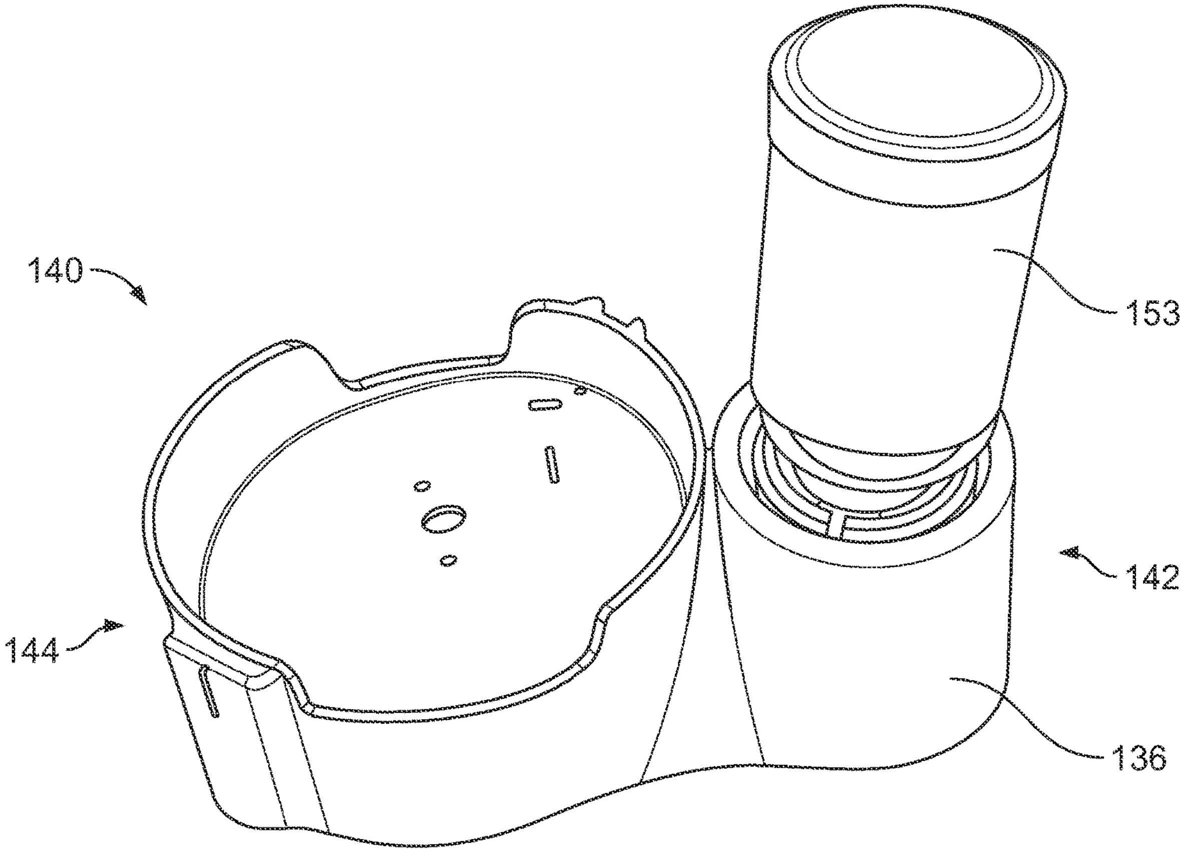
FIG. 9 is a perspective view of an embodiment of the transfer device of the disclosure and a vial containing a liquid medication.

In operation, a vial in an inverted orientation, as illustrated for vial 153 in FIG. 9, is placed into the vial elevator 148 when the vial elevator is in the raised or extended position (FIGS. 3-5B) until the downward surface formed by the septum or rim of the vial engages the stop pins 164*a*-164*d* (FIGS. 5A-6B) of the stop tabs 162*a*-162*d*. The user then gently presses down on the vial. As this occurs, the distal ends of the stop tabs 162*a*-162*d* of the vial elevator 148 are pushed downwards due to the downward-facing end surface (septum and/or vial rim) of the vial pushing downwards on the stop pins 164*a*-164*d*. As a result, the claws 155*a*-155*d* of the lock arms 154*a*-154*d* are free to move inwards.

As the user continues to press down on the vial, the vial elevator 148 moves downwards (in the direction of arrow 169 of FIG. 5A) into the stationary vial elevator shaft 146 towards the retracted position.

As the vial elevator 146 moves downwards towards the retracted position, the claws (155*a*-155*b* of FIGS. 6A and 6B) on the distal ends of the lock arms 154*a*-154*d* are moved inwards due to the urging of the elevator shaft cam ramps (170*a*-170*d* of FIG. 7). When the vial elevator 148 reaches the fully retracted position, the vial locking shoulders (178*a*-178*d* of FIGS. 5A-6B) of the lock arms 154*a*-154*d* have moved into a position where they engage the neck of the vial. In addition, each of the cam hooks 158*a*-158*d* (FIGS. 5*a*-6B) have engaged corresponding rectangular elevator locking loops, such as elevator locking loops 182*a* and 182*b* illustrated for cam hooks 158*a* and 158*b*. As a result, the vial elevator 148 is locked into the lowered or retracted position and the vial is locked within the vial holder 142.

As an example only, each vial can have a capacity of 1-50 mL with neck finishes of 13-20 mm.

If a user attempts to push the vial elevator 148 down into the vial elevator shaft 146 without a vial in the vial elevator, as mentioned previously, inward travel of the claws 155*a*-155*d* on the distal ends of the lock arms 154*a*-154*d* is prevented due to engagement with the distal ends of the stop tabs 162*a*-162*d* so as to prevent the vial elevator 148 from being moved into the retracted position. The spacing of the bottom of the passage plate (190 of FIGS. 5A and 5B) from the bottom of the vial elevator 148 is such that when the claws of the lock arms are in engagement with the stop tabs, the tip of the vial spike positioned on the bottom of the vial holder base is below the bottom of the vial elevator (i.e., the upwardly-pointing vial spike has not yet passed through the opening 166 of the elevator bottom). As a result, the user is protected from sticking his or her finger with the vial spike.

Figure 10B:
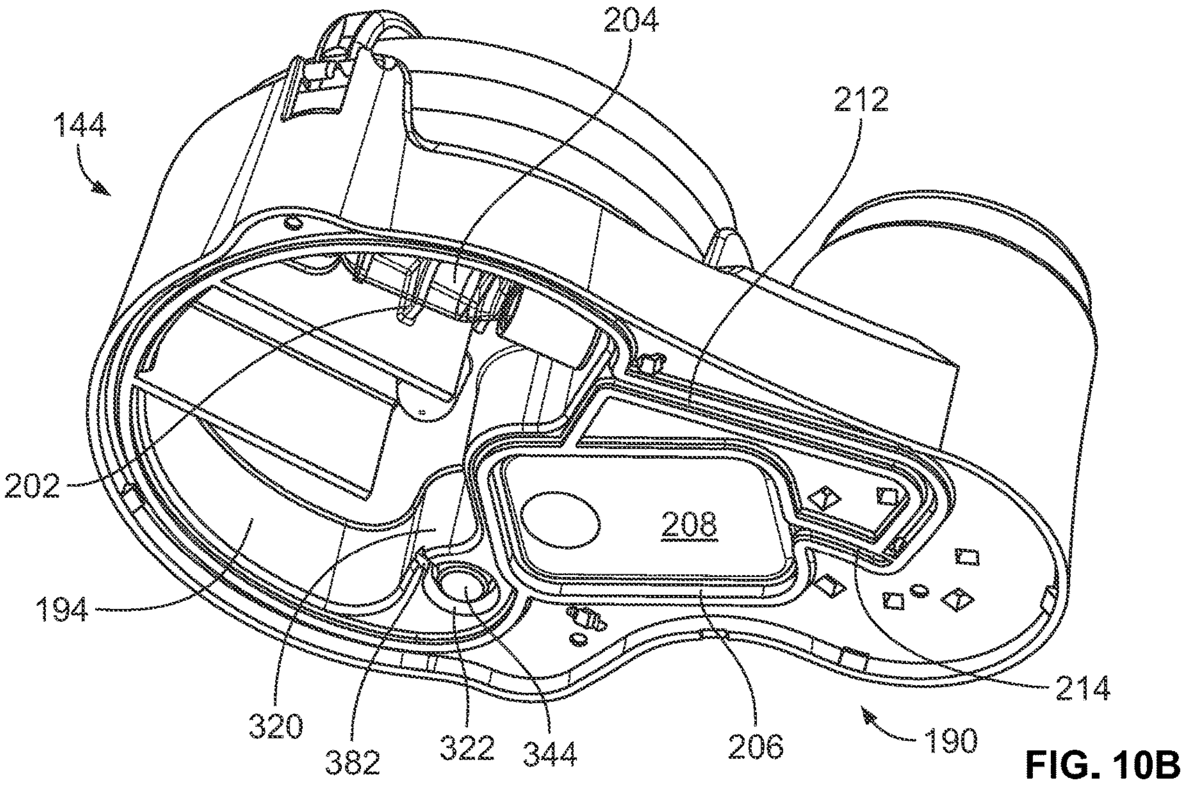
FIG. 10B shows the transfer device of FIG. 10A with the baseplate removed.

As illustrated in FIG. 10A, the baseplate 138 covers the bottom of the housing 136 of the transfer device 140. As illustrated in FIG. 10B, removal of the baseplate reveals a passage plate, indicated in general at 190, and a gas expansion chamber 194, where the latter serves as a source of pressurized gas for pressurizing the vial as will be described below.

As illustrated in FIG. 10B, the gas expansion chamber 194 is provided with brackets 202 configured to retain and support a gas cartridge 204 (shown in transparency in FIG. 10B) containing a compressed gas, such as compressed nitrogen. Of course, cartridges containing other types of compressed or pressurized gases may be used. As will be explained in greater detail below, the gas cartridge is punctured to provide pressurized air to drive liquid from a vial (153 in FIG. 9) to an injection device (103 in FIG. 3) that is connected to the transfer device 140.

The passage plate 190 is provided with a filter recess 206 for holding a filter 208 through which, as explained in greater detail below, fluid travels from the vial spike hub to an injection device mounted to the transfer device.

A gas passage 212 formed in the passage plate 190 as is a liquid passage 214. As an example only, the passage plate may be formed from plastic with the passages cut, molded or otherwise formed therein. The inlet of the gas passage 212 is in fluid communication with the gas expansion chamber 194, while the outlet of the liquid passage 214 is in fluid communication with the filter recess 206.

Integrating the gas and liquid passages 212 and 214 into the passage plate provides at least the advantages of manufacturing efficiency and shorter passage lengths. The latter reduces pressure drop of fluids traversing the passages and therefore permits lower pressure gas canisters to be used. This construction also facilitates scalability of the transfer device. As examples only, the baseplate, housing cover, passage plate and other components of the transfer device may be constructed out of plastic and secured together with laser bonding, ultrasonic welding or adhesive.

Figure 11:
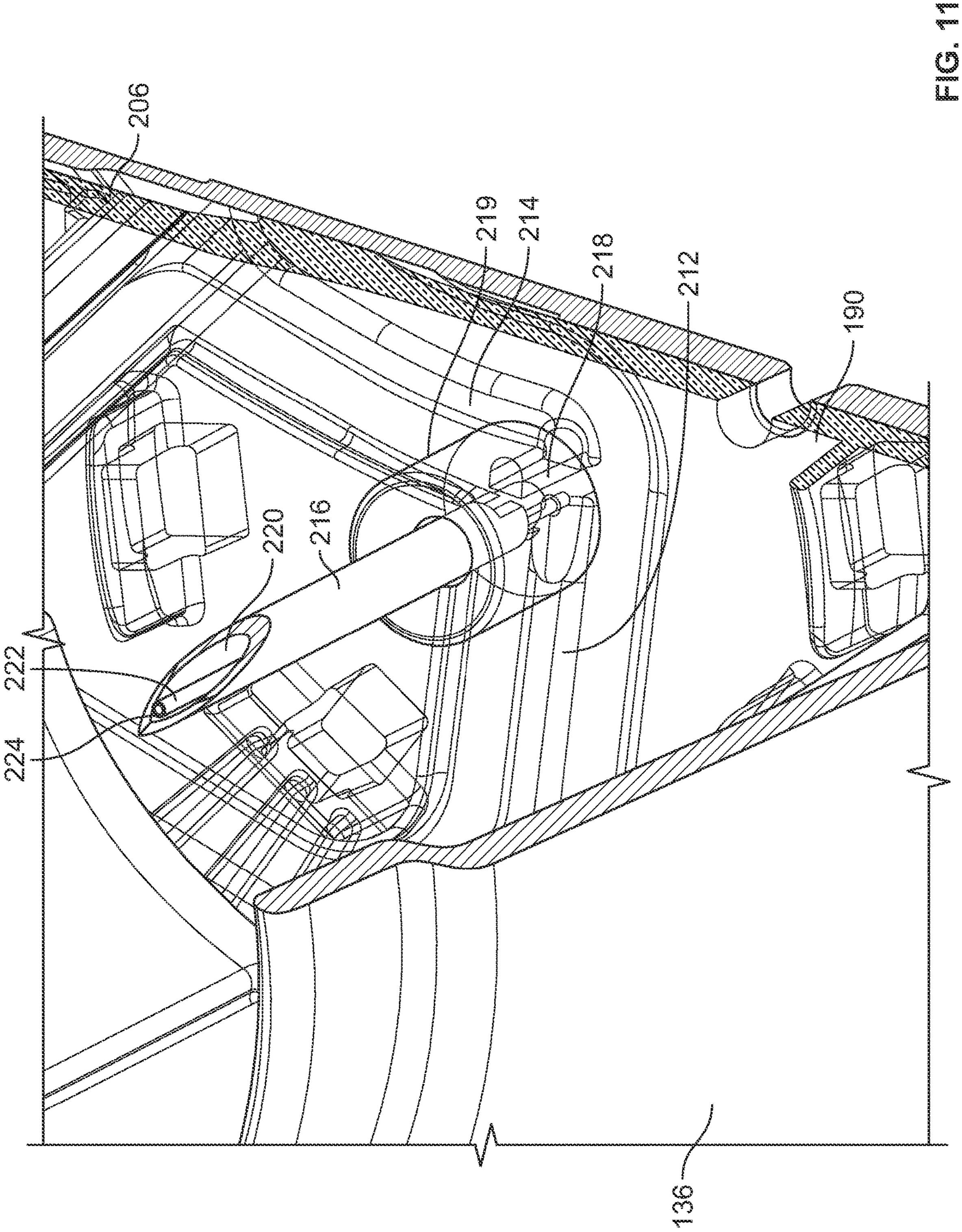
FIG. 11 is an enlarged partially transparent perspective view of the vial spike of the transfer device of FIGS. 3 and 4.
Figure 12:
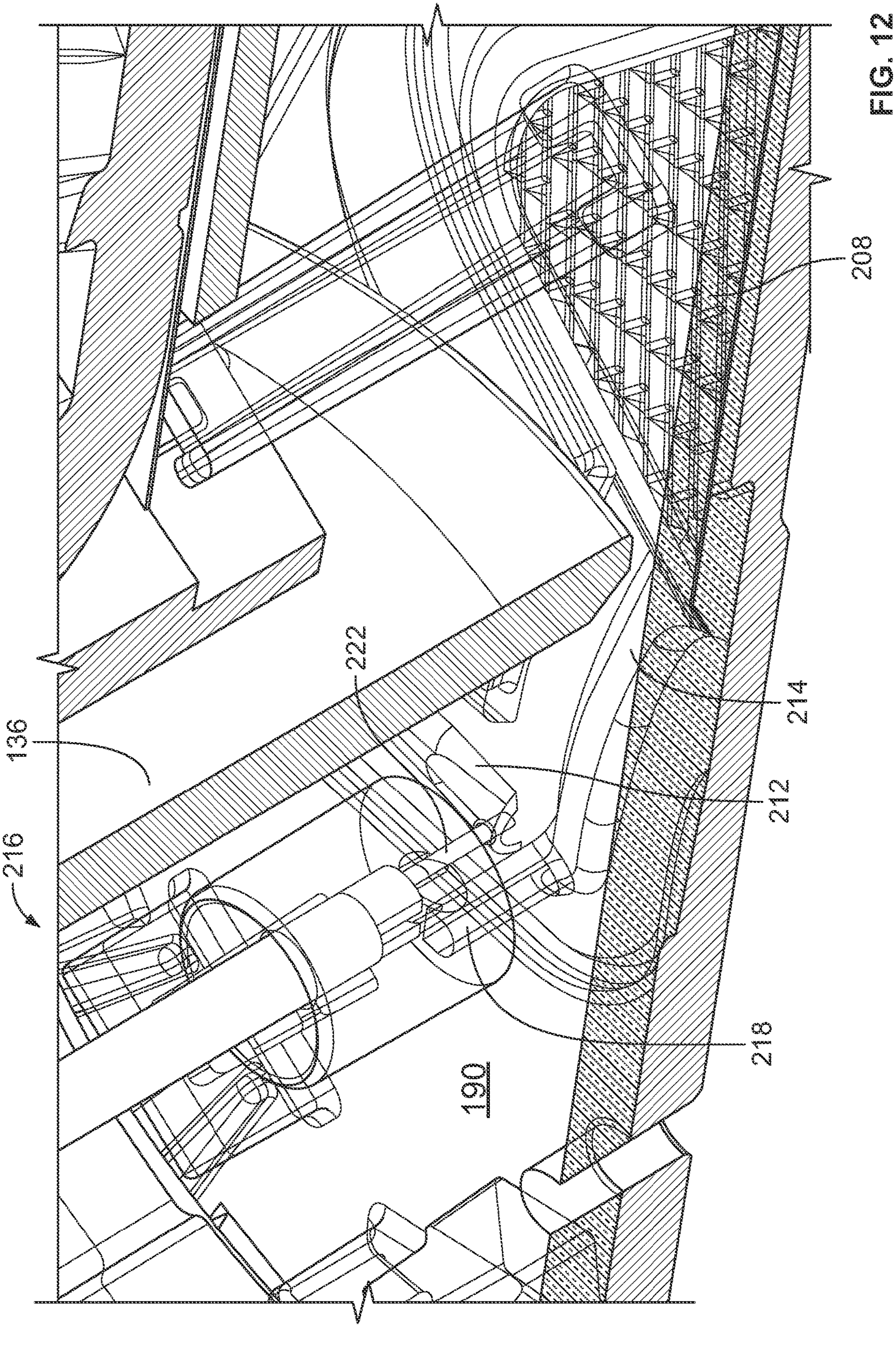
FIG. 12 is an alternative view of FIG. 11.

As illustrated in FIGS. 11 and 12, the inlet of the liquid passage 214 is in fluid communication with the lower end of a vial spike, indicated in general at 216, via duct 218. Duct 218 is located within a boss, illustrated at 219 in FIGS. 5B and 11, that is formed on the top surface of the passage plate 190 and positioned below the central portion of the vial elevator (148 of FIGS. 5A and 5B). The vial spike 216 is secured within a bore of the boss 219 via adhesive to prevent fluid "short circuits" with regard to the gas passage 212. The vial spike 216 may take the form of a cannula, which is preferably constructed from stainless steel, having a pointed tip that forms a liquid opening 220.

A gas tube 222 features a gas outlet opening 224 and extends through the vial spike 216. The lower end of the gas tube 222 is secured within the passage plate 190 and is in fluid communication with the outlet of the gas passage 212. As an example only, the gas tube may be constructed from polyimide.

In order for incoming gas from the gas tube 222 to reach the headspace of a vial, locked within the device in the manner described above, it should be able to pass by the liquid opening 220 of the vial spike and reach the top surface of the liquid drug in the vial. As a result, as illustrated in FIG. 11, the gas tube opening 224 is positioned generally higher than the liquid opening 220 of the vial spike 216.

In an alternative embodiment, two separate spikes with independent lumens may be used as the vial spike and the gas tube.

The pointed tip of the vial spike 216 passes through the vial diaphragm or septum when the vial elevator 148 of FIGS. 5A-6B is moved into the lowered and retracted position (whereby the vial spike passes through the central opening 166 of the vial elevator). The vial spike 216 and the gas tube 222 provide two fluid paths—one to permit entry of compressed gas to force the liquid out of the vial, and one for the exiting liquid to the injection device.

After the vial spike and gas tube are fully positioned within the vial, pressurized air from the punctured compressed gas cartridge 204, the gas expansion chamber 194 (FIG. 10B) and then gas path 212 is released into the vial headspace through the gas tube 222 and gas tube opening 224. The tip of the gas tube 222 featuring the gas outlet opening 224 is generally higher than the fluid outlet opening 220 in the vial spike 216, thus allowing the air to bubble up through the liquid drug and into the headspace or closed end of the vial.

Liquid medication in the vial is forced by pressurized gas to exit through the vial spike opening 220, duct 218 and out through liquid passage 214 to the lower portion or inlet side of the vent recess 206.

Figure 13:
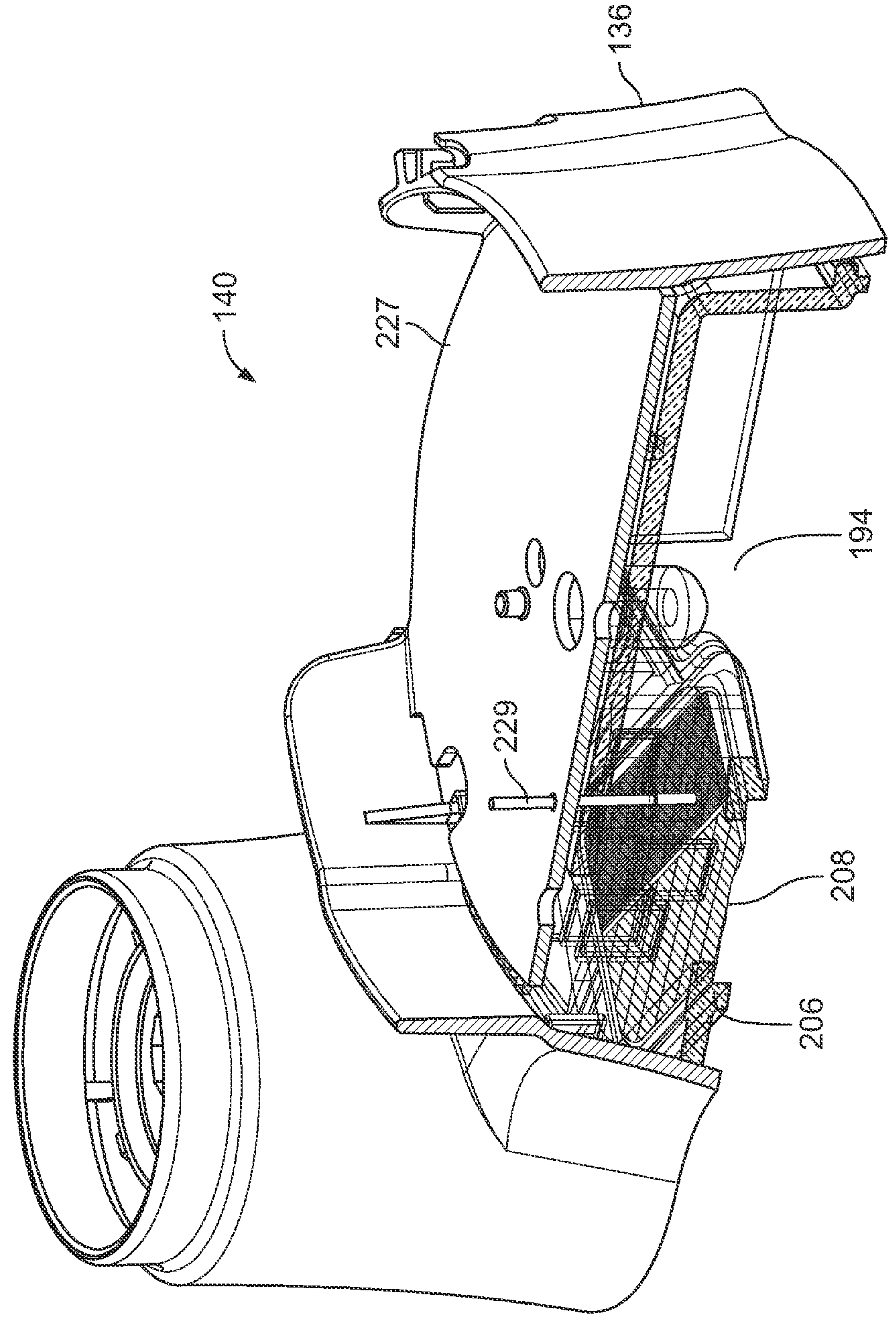
FIG. 13 is a partially transparent sectional view of the transfer device of FIG. 4.

With reference to FIG. 13, the housing 136 of the transfer device 140 includes an injection device support surface 227. An injection device port, such as transfer cannula 229, passes through the injection device support surface 227. A top end portion of the transfer cannula 229 enters a fill port of an injection device positioned on the injection device support surface (as illustrated by injection device 103 of FIG. 3). The bottom end portion of the transfer cannula 229 is in fluid communication with the upper or outlet side of the filter recess 206. As an example only, the transfer cannula may be a 19 gauge tube having a filleted edge that reduces the risk of damaging a fill septum of the injection device.

With continued reference to FIG. 13, the vent filter 208 is used to vent the front end and back end air from the system during the transfer of drug, keeping air from entering the injection device. More specifically, as explained above, a pressurized canister is punctured and is used as the driving force to push liquid and air from a vial. The empty liquid passage 214 between the vial spike 216 and the filter recess (and thus filter 208) is filled with front end air that should be vented from the system before liquid can be pushed into the injection device.

With reference to FIG. 10A, the filter recess is provided with an air outlet port 231, which is formed in a filter recess cover 233. As explained in PCT International Application Publication No. WO 2016/154413 (incorporated by reference above), the filter 208 (FIG. 13) includes a hydrophilic membrane and a hydrophobic membrane, with a fluid chamber positioned there between. The filter recess 206 receives fluid from the liquid passage 214. As a result, the front end air trapped in the fluid path passes through the hydrophobic membrane of the filter 208 and out of the air outlet port 231 and into the atmosphere. The filtered liquid passes through the hydrophilic membrane of the filter 208, out through the transfer cannula 229 and into the injection device.

The front end air is vented due to the inherent flow restriction of the hydrophilic membrane, coupled with the pressure required to fill the injection device. These factors force the front end air to find the path of least resistance when being sent through the filter 208, and that is through the hydrophobic membrane and through air outlet port 231 (FIG. 10A) rather than through the restrictive hydrophilic membrane and into the injection device. The hydrophilic membrane of the vent filter allows liquid to pass through it and enter the injection device. Once the hydrophilic membrane is wetted by the liquid, it will not allow air to pass through it, only liquid, thus keeping the air from entering the injection device. The hydrophilic filter also has the capability of not only filtering air but also aggregate or particulate from the drug product from being transferred into the injection device.

Once all of the liquid is transferred to the injection device, residual air pressure still exists in the transfer device, including in the gas expansion chamber 194. This air enters the filter 208 and is blocked by the hydrophilic membrane and exits out of the filter recess 206 into the atmosphere through the hydrophobic membrane. This process continues until a specified pressure is reached within the gas expansion chamber, and a pressure relief assembly, described below, vents the remaining pressure in the system.

As indicated previously, the gas expansion chamber 194 is pressurized when the gas cartridge 204 (FIG. 10B) positioned therein is punctured. The cartridge puncture mechanism for doing so will now be described.

Figure 14A:
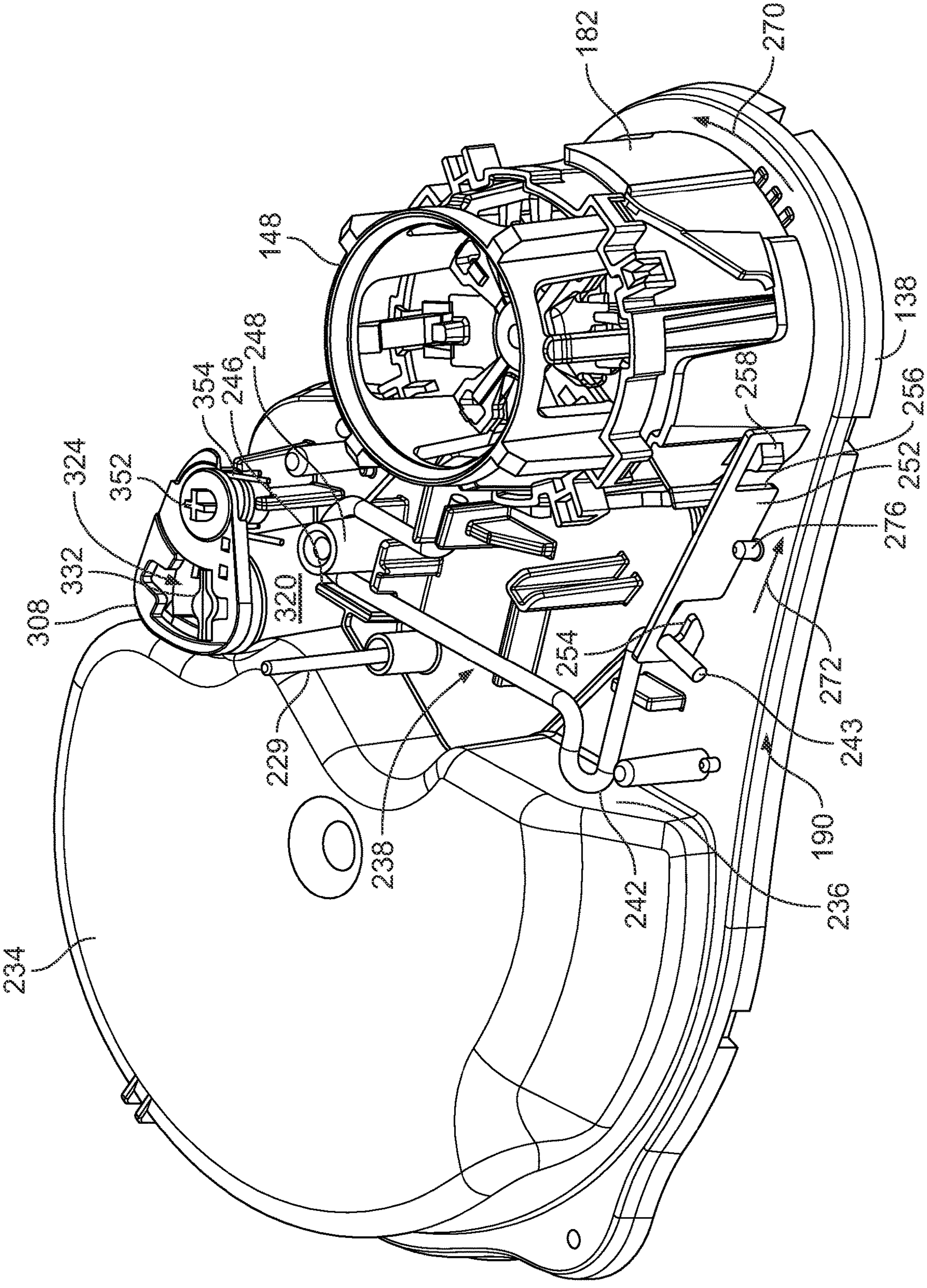
FIG. 14A is a perspective view of the transfer device of FIGS. 3 and 4 with the housing cover removed.

With reference to FIG. 14A, a gas expansion chamber housing 234 includes a flexible wall portion 236. As an example only, the flexible wall portion 236 may be constructed of plastic with a thickness of approximately 0.030" for flexibility.

A trigger spring, indicated in general at 238, includes a hammer portion 242 and a latch portion 243 on the distal end and a multi-curved retainer portion 244 on the proximal end. A bracket 246 and a retainer post 248 formed on the passage plate 190 cooperate to secure the retainer portion of the proximal end of the trigger spring in place in a fixed manner. The hammer portion 242 is urged into engagement with the flexible wall portion 236 of the gas expansion chamber housing 234 by the resilient forces of the trigger spring, as illustrated in FIG. 14A. As examples only, the trigger spring 238 may be made of metal or steel.

With continued reference to FIG. 14A, a link 252 includes a first notch 254 and a second notch 256. The first notch 254 is engaged by the latch portion 243 on the distal end of the trigger spring 238. The second notch 256 is engaged by a link hook 258 formed on or secured to the cam ring 182. As an example only, the link may be made of steel, metal or plastic.

Figure 14B:
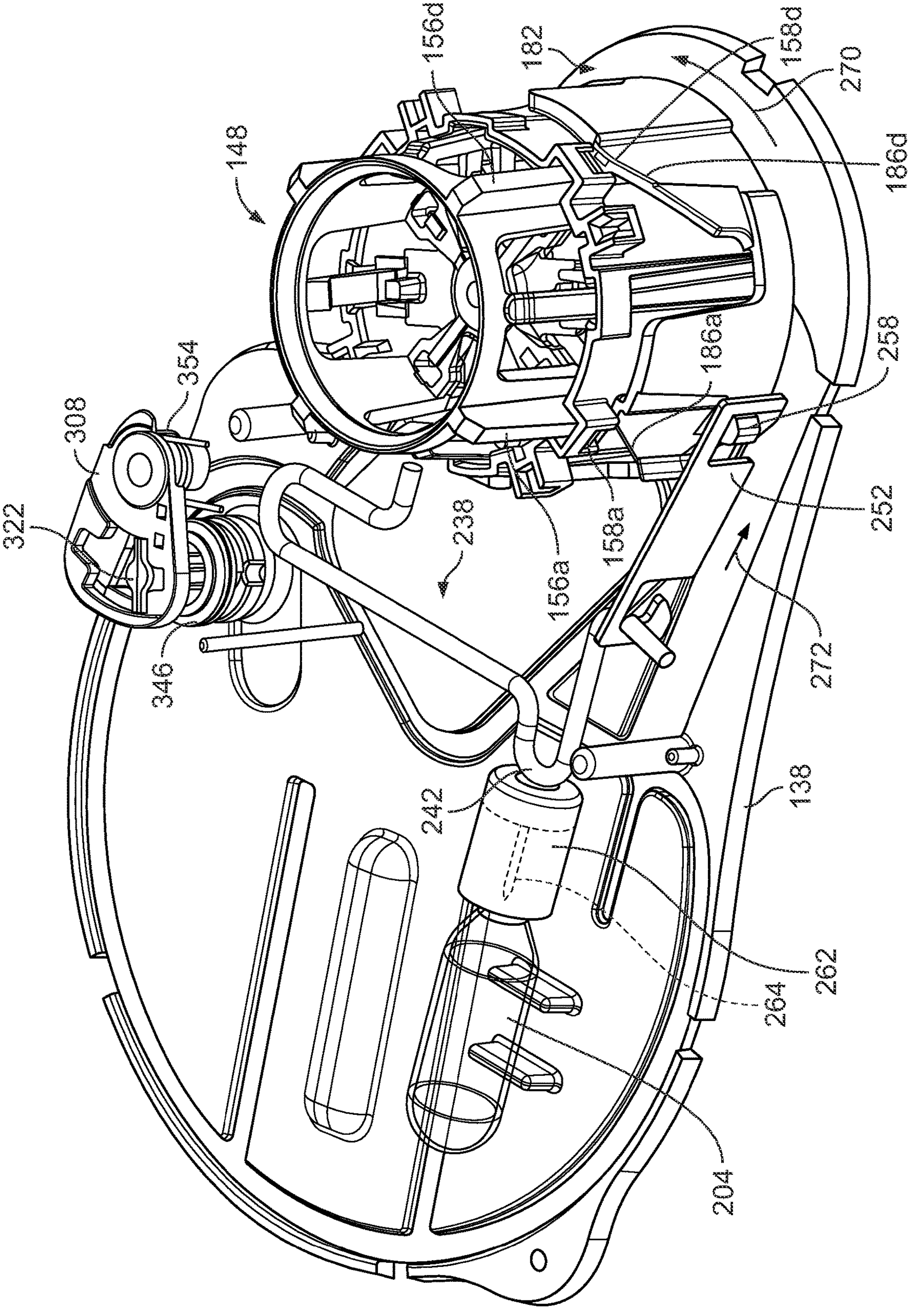
FIG. 14B shows the transfer device of FIG. 14A with the expansion chamber housing removed.

As illustrated in FIG. 14B, a gas cartridge cap 262 features an inner surface that holds a puncture tip, indicated in phantom at 264, having a sharp point. The cap 262 holds the puncture tip 264 in a position where the puncture tip opposes a seal of the pressurized gas cartridge 204.

As revealed by a comparison of FIGS. 14A and 14B, the cap 262 is positioned adjacent to, and in engagement with, an inner surface of the flexible wall portion 236 at a location that corresponds to the location where the hammer portion 242 of the trigger spring engages the flexible wall portion. As a result, the flexible wall portion 236 is sandwiched between the pressurized gas cannister cap 262 and the hammer portion 242 of the trigger spring 238.

As described previously, as illustrated in FIG. 14B, when the vial elevator is in the raised or extended position, the camming hook 158*a* of spline 156*a* is positioned at the top of the camming surface 186*a* of the cam ring 182 and the camming hook 158*d* of spline 156*d* is positioned at the top of the camming surface 186*d*. The camming hooks 158*b* and 158*c* (FIGS. 6A and 6B) of splines 156*b* and 156*c* are in the same position with respect to camming surfaces 186*b* and 186*c* (FIG. 8).

As a vial is inserted in the vial elevator (148 of FIGS. 4-6), and pushed down, so that the vial elevator 148 lowers and retracts into the vial elevator shaft 146, the spline hooks 158*a*-158*d* of the vial elevator travel down the corresponding camming surfaces 186*a*-186*d* of the cam ring so that the cam ring rotates in the direction of arrow 270 of FIGS. 14A and 14B (i.e. counterclockwise).

As the cam ring rotates in the direction of arrow 270 (FIG. 14B), the link 252 is pulled in the direction of arrow 272 in FIGS. 14A and 14B by the hook 258 of the cam ring 182. As a result, the hammer portion 242 of the trigger spring is pulled away from the flexible wall portion 236 of the gas expansion chamber housing against the urging of the trigger spring. This occurs until the latch portion 243 of the trigger spring slides out of the first notch 254 of the link 252 so that the deflected hammer portion 242, which is now spaced from the flexible wall portion 236, is released.

The released hammer portion 242, due to the resilient forces acting on the deflected trigger spring, impacts the flexible wall portion as the hammer portion springs back to its original position. This forces the central area of the flexible wall portion 236, and thus the puncture tip 264 of FIG. 14B, to move inwards and puncture the seal of the pressurized gas cartridge 204. In doing so, the flexible wall portion elastically deforms in a concave fashion (when viewed from outside of the gas expansion chamber housing 234). As a result, pressurized gas from the gas cartridge fills the gas expansion chamber and flows to the gas tube 222 (FIG. 11) via gas passage 212, as described above.

It should be noted that in alternative embodiments, the flexible wall may be used to propel the gas cartridge towards a stationary puncture tip to puncture the seal of the pressurized gas cartridge.

The shape and volume of the gas expansion chamber 194 (FIG. 10B) are such that the pressure of the gas provided to the gas tube 222 (FIG. 11) via gas passage 212, and thus to a vial positioned in the lowered or retracted vial elevator, is less than the pressure of the gas in the gas cartridge 204 (FIG. 14B). As a result, the internal cavity 194 acts as a pressure regulator.

With reference to FIG. 14A, a tuning post 276 is optionally provided on the passage plate 190 and is engaged by the side of the link 252 as it is pulled by the hook 258 of the cam ring 182 in the manner described above. As a result, the tuning post deflects the link 252, which is preferably elastic, as the link moves and thus impacts the release of the latch portion 243 of the trigger spring by notch 254. The positioning of the tuning post 276 may therefore be adjusted to fine tune the release point of the trigger spring hammer portion 242 in relation to the retraction of the vial elevator 148 (and thus a vial positioned therein) into the vial elevator shaft 146.

Figure 15:
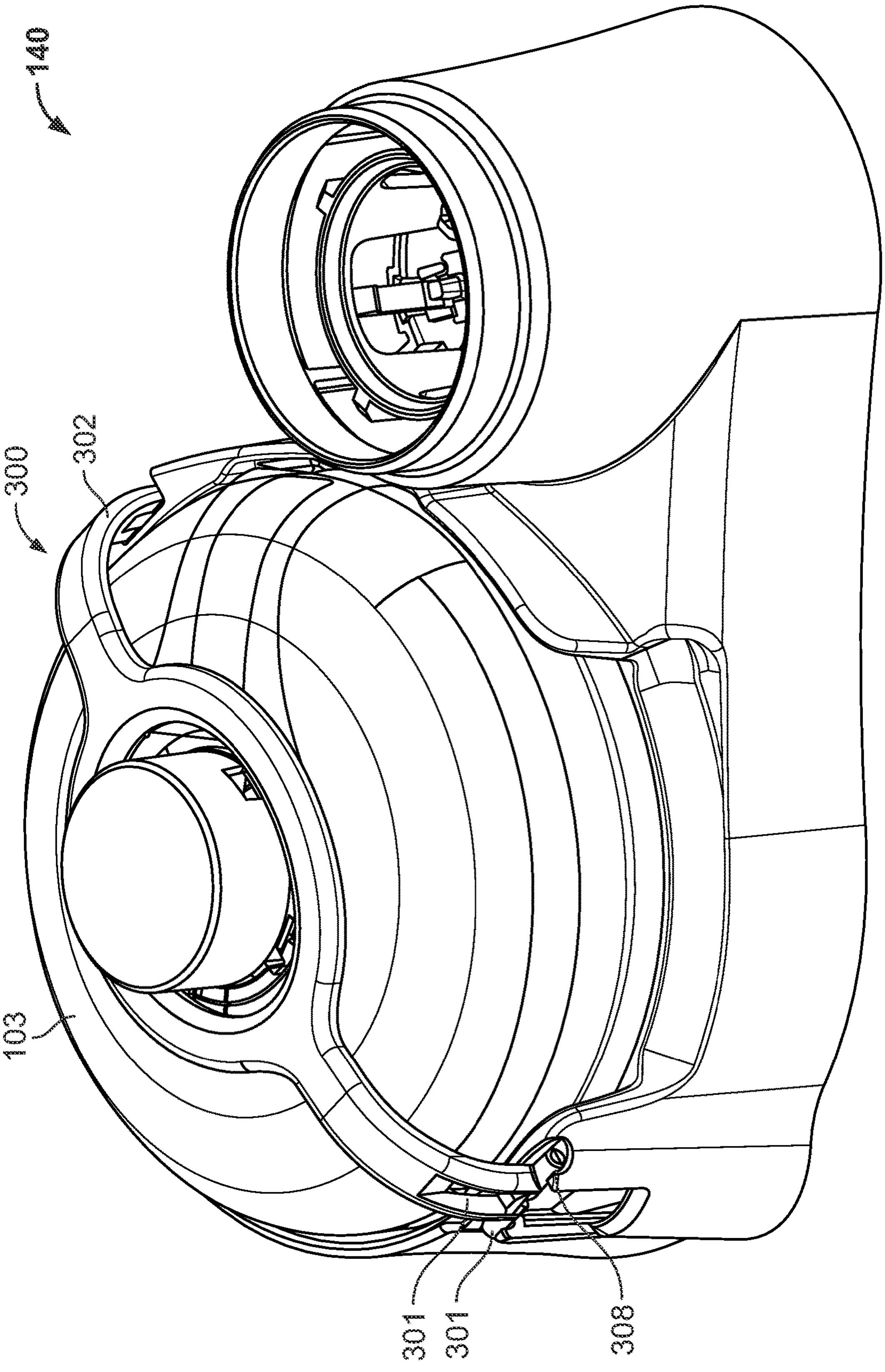
FIG. 15 is an alternative perspective view of the transfer device of FIG. 3.

As illustrated in FIGS. 3 and 15, a retainer strap, indicated in general at 300, holds the injection device 103 on the transfer device 140 during transportation. In addition, the retainer strap 300, as explained below, remains latched during the transfer of drug from the vial to the injection device 103. Once all of the drug is transferred to the injection device, the retainer strap 300 is released automatically, showing the user that the injection device is ready to be placed on the body.

In addition, a final venting from the transfer device 140 is performed that releases residual pressure inside the gas expansion chamber 194 (FIG. 10B) that remains after the drug has been completely transferred to the injection device 103. This feature prevents the user from removing the injection device from the transfer base too early. Without the strap, the user may be tempted to remove the injection device before all of the drug has been transferred out of the vial. The mechanism that performs these functions will now be described.

Figure 16:
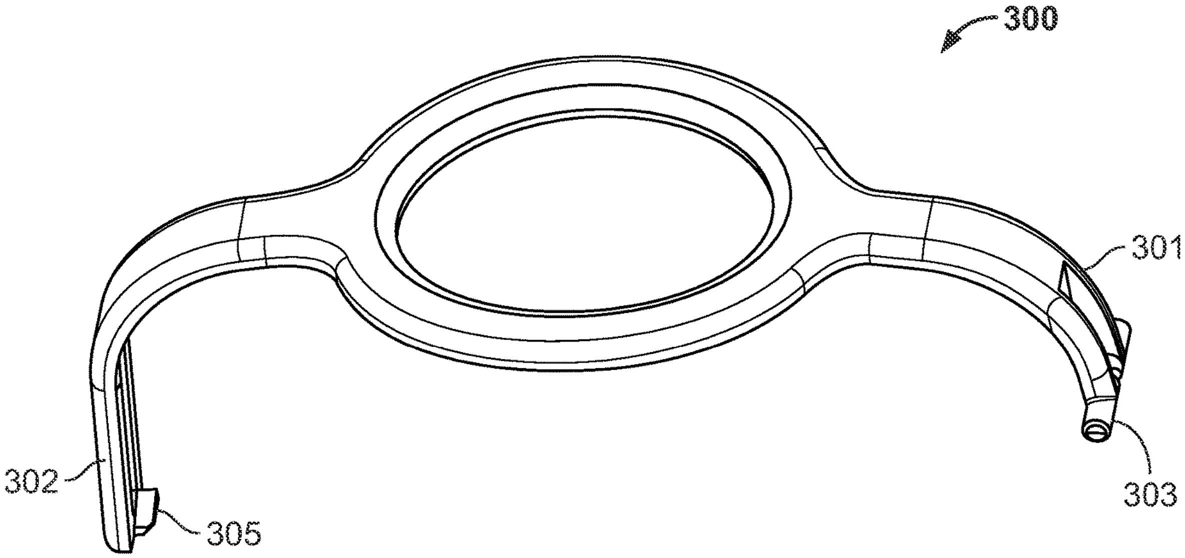
FIG. 16 is an enlarged perspective view of the retainer strap of FIG. 15.

As illustrated in FIG. 16, the retainer strap 300 includes a first end 301 having a pair of hinge pins 303 and a second end 302 featuring a latching hook 305. As illustrated in FIG. 15, the hinge pins 303 are received within a hinge pin receptacle 308 so that the hinge pins 303 are free to rotate therein. As an example only, the hinge pins may be secured within the hinge pin receptacle in a snap-fit manner.

Figure 17:
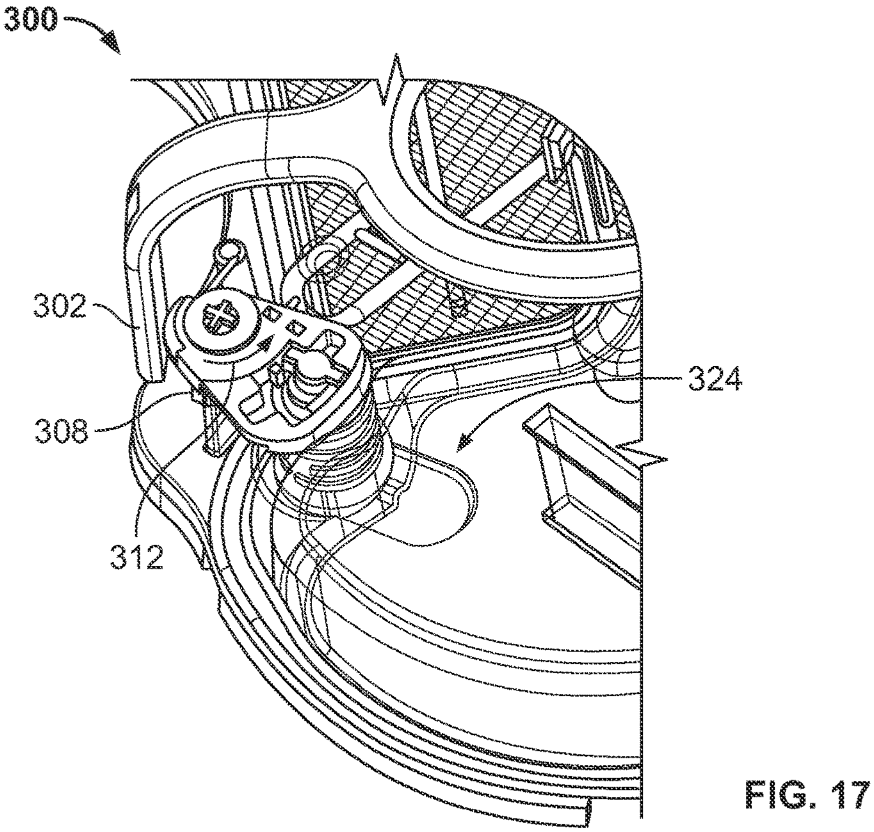
FIG. 17 is an enlarged perspective view of the pressure relief piston assembly, the pivot plate and a portion of the retainer strap of the transfer device of FIGS. 3, 4 and 15.

As illustrated in FIG. 17, the latching hook of the second end 302 is secured in the latched position illustrated in FIGS. 3 and 15 by a pivot plate 308. As will be explained below, the pivot plate 308 is pivoted from the position illustrated in FIG. 17 in the direction of arrow 312 (i.e. counterclockwise) during venting of air pressure from the transfer device to release the latching hook 305 (FIG. 16) of the retainer strap 300 so that the injection device may be removed from the transfer device for use.

Figure 18:
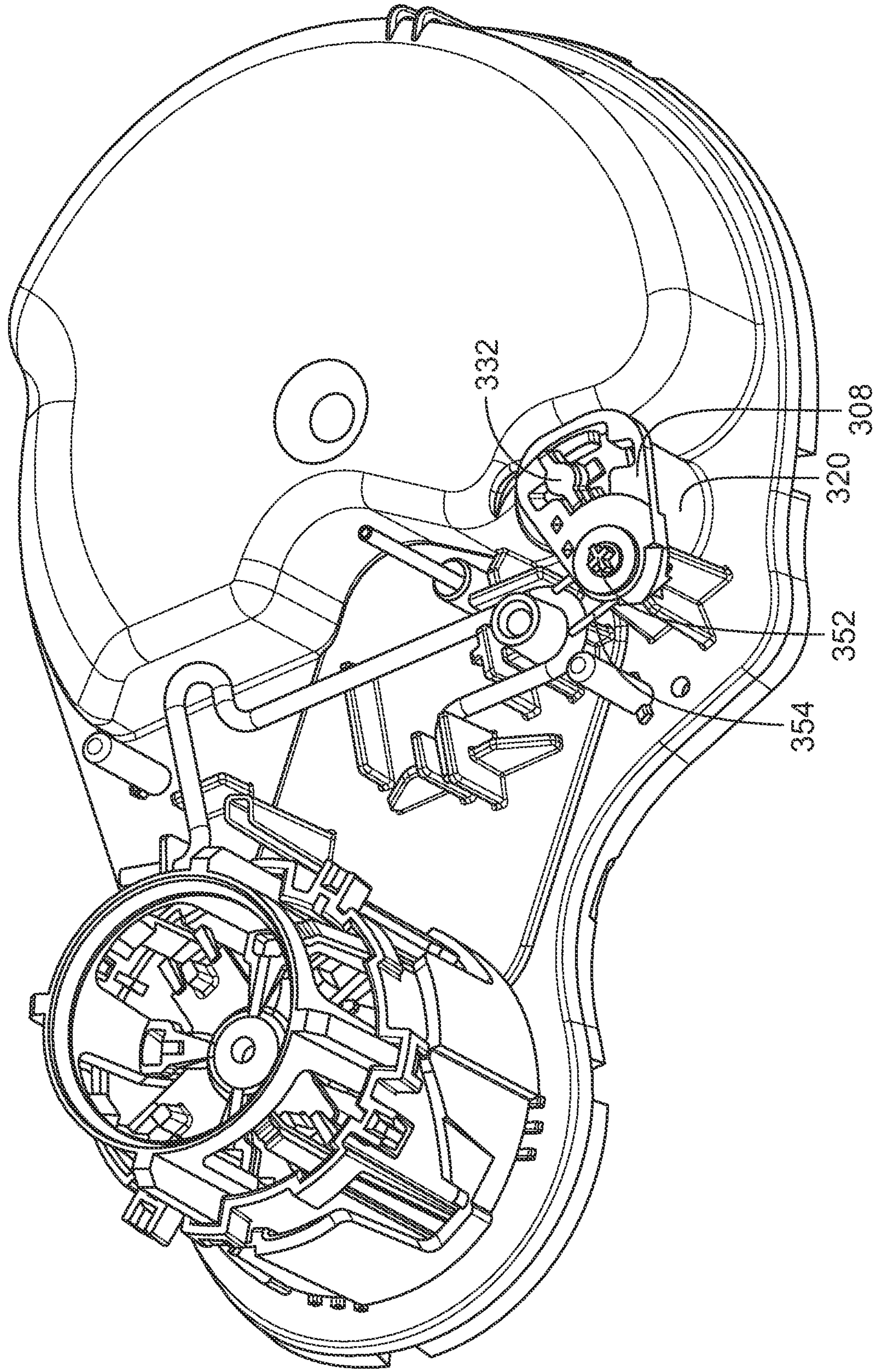
FIG. 18 is an enlarged perspective view of the transfer device of FIG. 3 with the housing cover removed.

As illustrated in FIGS. 10B and 18, the expansion chamber 194 is provided with a vent housing 320. The vent housing includes a pressure relief or venting bore indicated at 322 in FIGS. 10B, 19 and 20.

Figure 22:
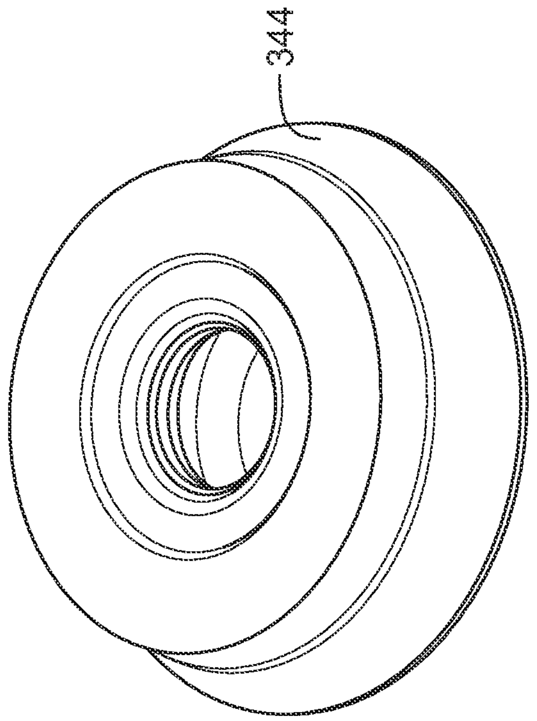
FIG. 22 is an enlarged perspective view of the sealing ring of the pressure relief piston assembly of the transfer device of FIGS. 3, 4 and 15.
Figure 21:
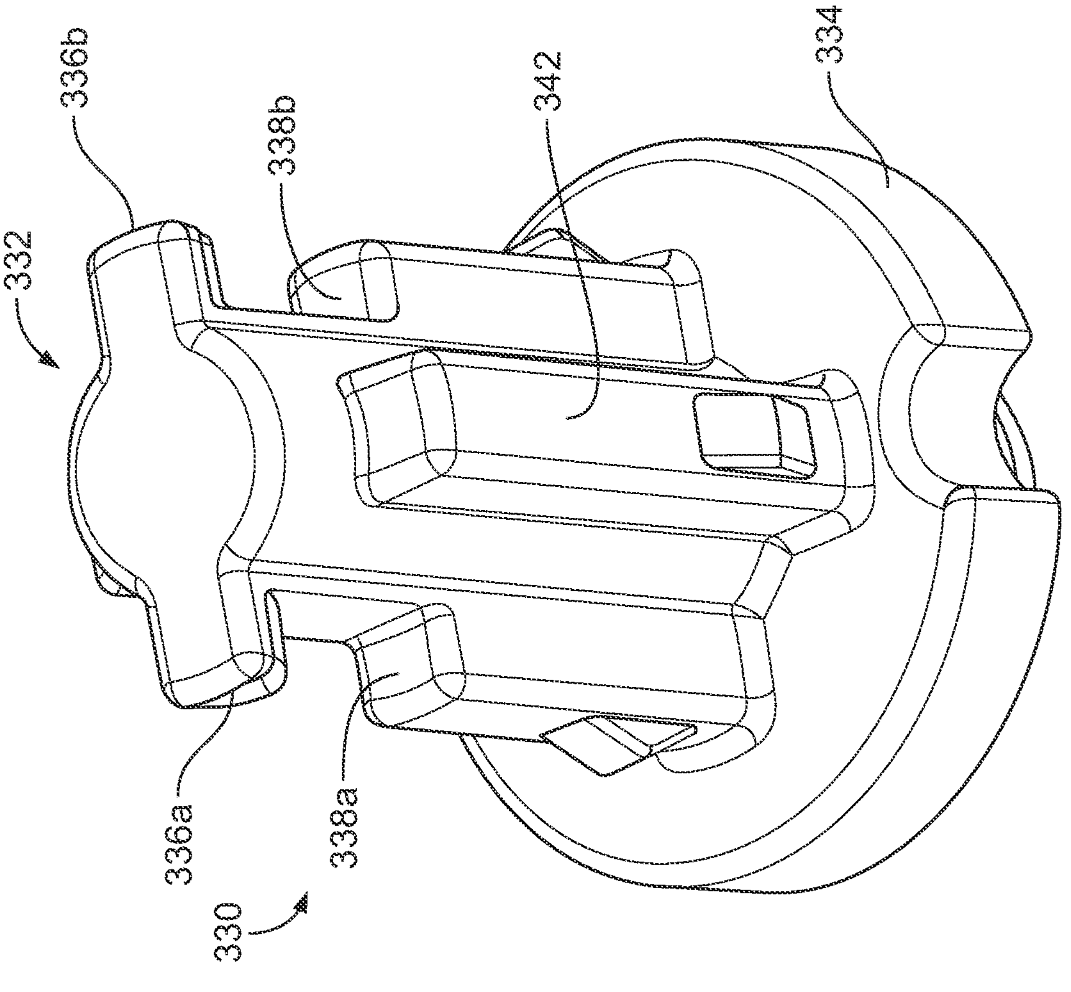
FIG. 21 is an enlarged perspective view of the core of the pressure relief piston assembly of the transfer device of FIGS. 3, 4 and 15.
Figure 23:
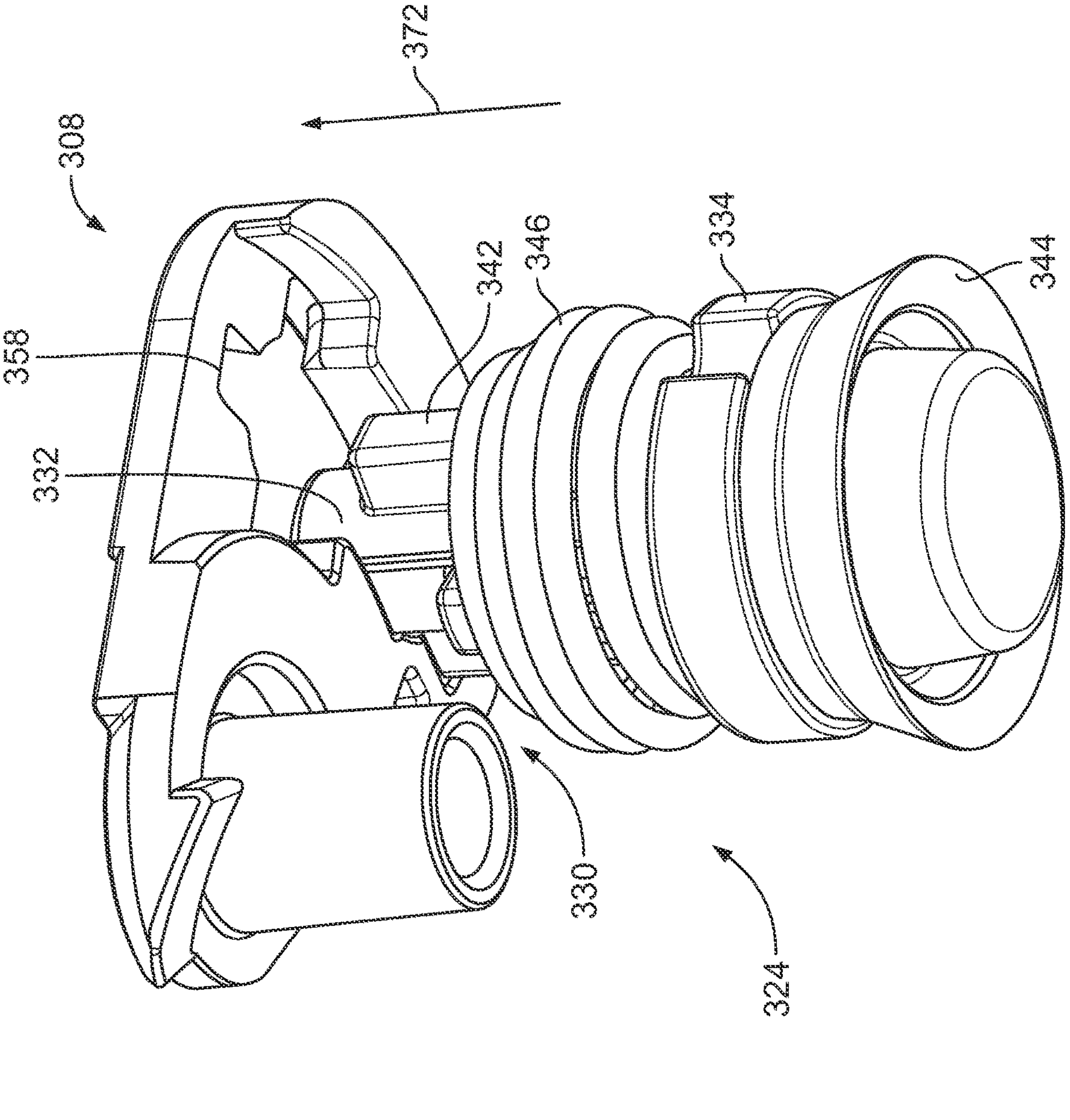
FIG. 23 is a perspective view of the pressure relief piston assembly of the transfer device of FIGS. 3, 4 and 15.

As illustrated in FIGS. 14A and 17, a pressure relief piston assembly, indicated in general at 324, is positioned within the vent housing 320 pressure relief bore. The pressure relief piston assembly includes a core, indicated in general at 330 in FIG. 21, having a head 332 (also shown in FIGS. 14A, 18, 23 and 25) and a flange 334. With reference to FIG. 21, the head 332 includes a pair of ear tabs 336*a* and 336*b*, as well as shoulders 338*a* and 338*b* and a stop 342. With reference to FIGS. 22 and 23, a sealing ring 344 is attached to a bottom portion of the core below flange 334. As illustrated in FIGS. 14B and 23, a compression coil spring 346 is also positioned around the core above the flange 334.

Figure 19:
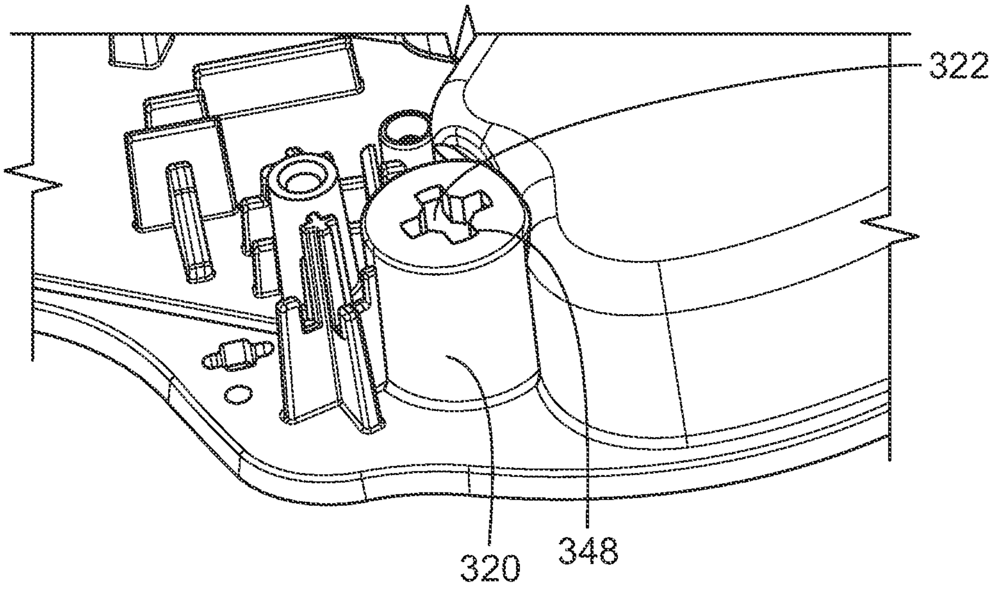
FIG. 19 is an enlarged to perspective view of the vent housing and venting bore of the transfer device of FIG. 18 with the pivot plate and the pressure relief piston assembly removed.

The pressure relief piston assembly 324 is attached to the vent housing 320 by inserting the piston assembly head-first through the bottom opening of the bore 322 (visible in FIG. 20) and passing the ear tabs 336*a* and 336*b* (FIG. 21) up through the corresponding portions of the cross-shaped top opening 348 of the vent housing illustrated in FIG. 19. As a result, with reference to FIG. 23, the compression coil spring 346, the flange 334 and the sealing ring are all positioned within the bore of the vent housing.

Figure 24:
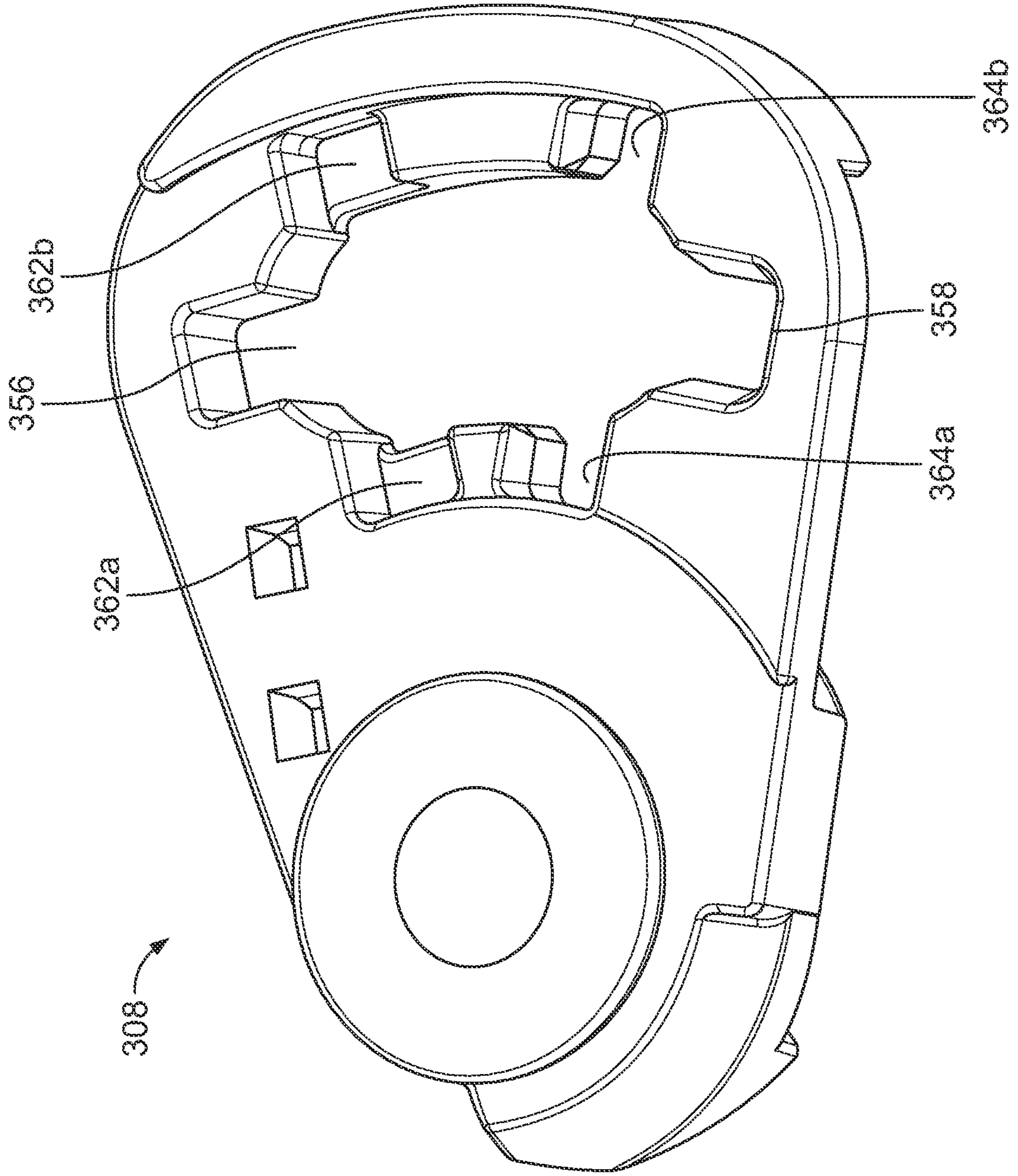
FIG. 24 is an enlarged top perspective view of the pivot plate of the transfer device of FIGS. 3, 4 and 15.

As illustrated in FIGS. 14A and 18, the pivot plate 308 mentioned previously is pivotally attached to a mounting post 352 positioned next to the vent housing 320. A torsion spring 354 is also positioned upon the mounting post 352 and urges the pivot plate 308 to rotate in the counterclockwise direction (arrow 374 in FIG. 25). As shown in FIG. 24, the pivot plate includes an arcuate main slot 356 having a stop wall 358, an opposing pair of recesses 362*a* and 362*b* and an opposing pair of slots 364*a* and 364*b*.

Figure 25:
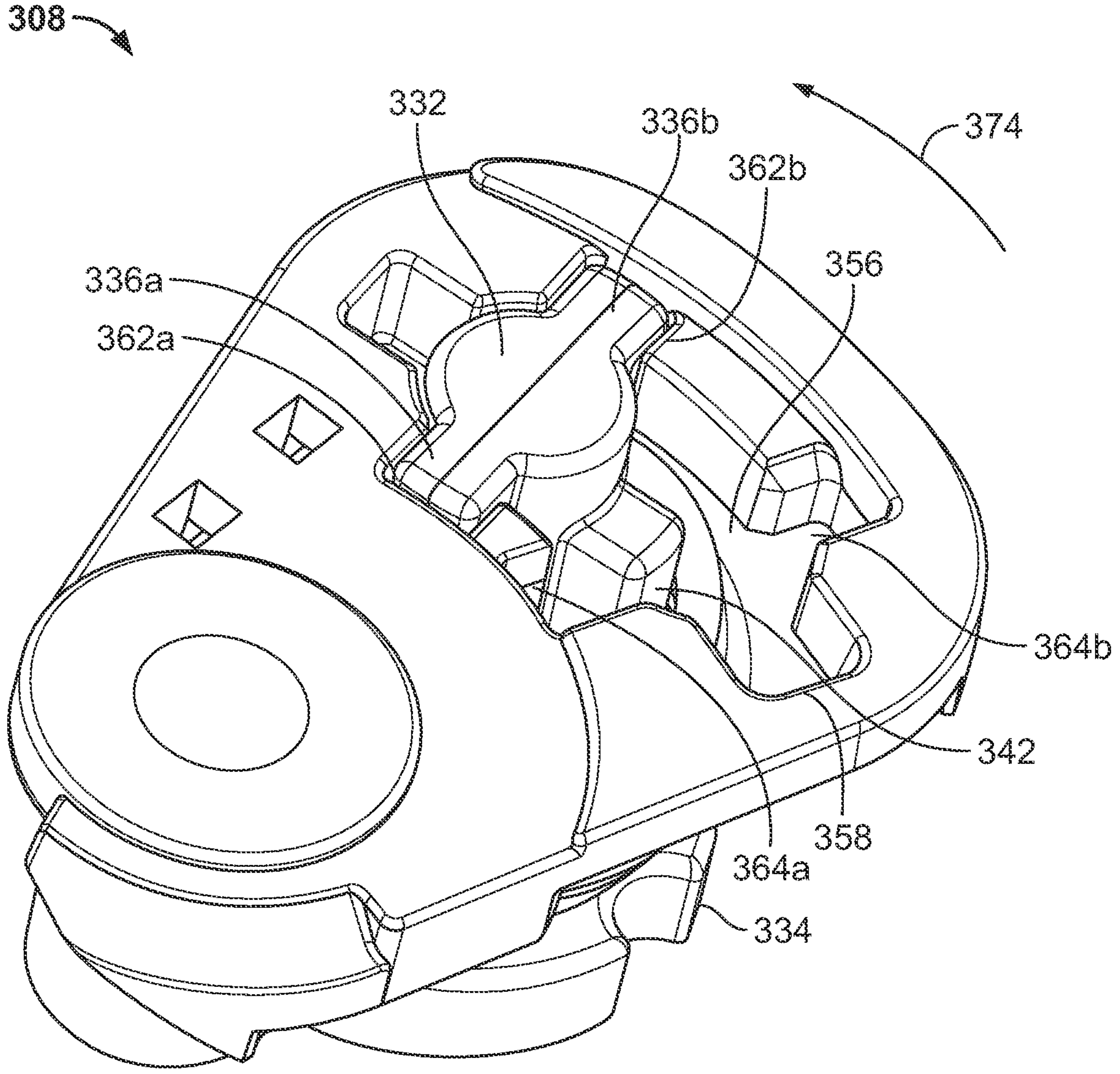
FIG. 25 is an top perspective view of the pressure relief piston assembly and the pivot plate of FIGS. 23 and 24.

As illustrated 14A and 18, the arcuate main slot 356 overlays the top of the vent housing 320 with, as also shown in FIG. 25, the head 332 of the piston assembly positioned within the elongated slot 356 and the arms 336*a* and 336*b* of the piston assembly initially positioned within the recesses 362*a* and 362*b* of the pivot plate 308 due to the urging of compression coil spring 346 of FIG. 23. As illustrated in FIG. 10B, the sealing ring 344 is positioned within and closes the venting bore 322 when the pressure relief assembly is in this configuration, which corresponds to the transfer device before the pressurized gas cartridge in the expansion chamber is punctured.

The transfer device 140 prior to use, and with an injection device 103 positioned thereon and secured thereto by retainer strap 300, is illustrated in FIGS. 3 and 15. The configuration of the pressure relief piston assembly 324 and pivot plate corresponding to the transfer device initial condition illustrated in FIGS. 3 and 15 is illustrated in FIGS. 14A, 18, 23 and 25.

The user next inserts and pushes a vial containing liquid mediation into the vial elevator of the transfer device and moves it towards the retracted position so as to activate the transfer device and initiate the transfer of drug from the vial into the injection device.

As described above, the act of pushing the vial into the system causes the pressurized gas cartridge (204 of FIGS. 10B and 14B) to be punctured, thus filling the pressurized gas expansion chamber 194 (FIG. 10B) with pressurized gas. This pressure in the gas expansion chamber pushes on the bottom of the sealing ring 344 (FIGS. 10B and 23) which forces the piston assembly to raise in the direction of arrow 372 of FIG. 23 against the urging of the piston assembly compression spring 346. As a result, with reference to FIG. 25, the arms 336*a* and 336*b* of the piston assembly rise up out of the recesses 362*a* and 362*b* (FIG. 24) of the pivot plate 308. The pivot plate 308 then rotates due to the urging of the torsion spring 354 (FIGS. 14A and 18) in the direction of arrow 374 of FIG. 25 until the stop 342 of the piston assembly contacts the stop wall 358 of the pivot plate 308. At this point, the sealing ring 344 is still positioned within the venting bore 322 and the venting bore remains closed as the transfer liquid medication from the vial to the injection device occurs. In addition, with reference to FIG. 17, the latching hook of the retainer strap 300 remains in engagement with the pivot plate 308 so that the retainer strap prevents removal of the injection device from the transfer device during the transfer of the liquid medication.

Figure 20:
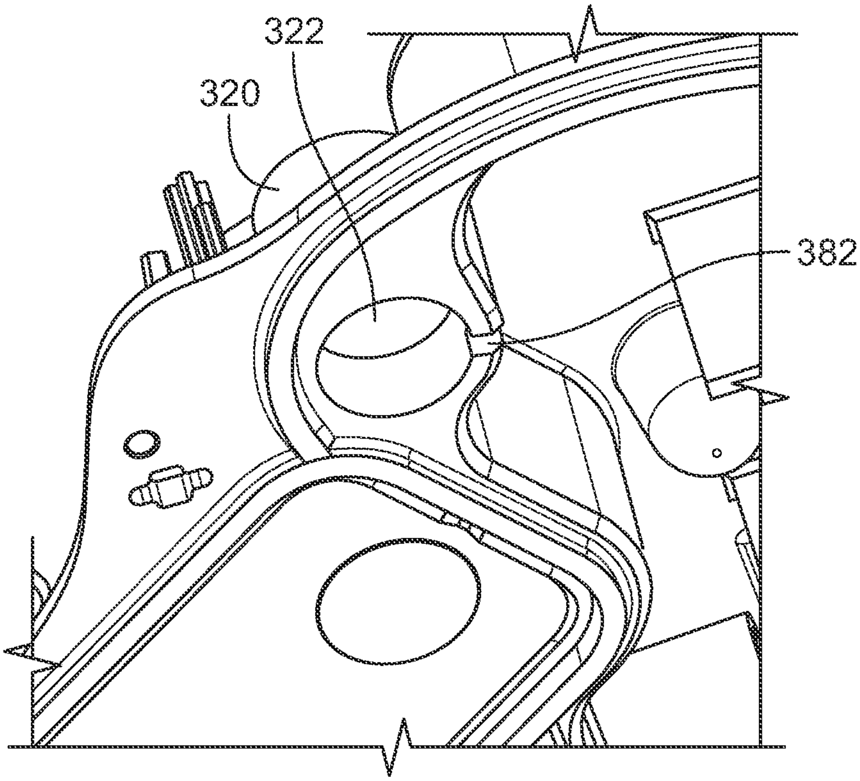
FIG. 20 is a bottom perspective review of the vent housing and venting bore of FIG. 19.

Once the transfer of fluid to the injection device is completed, the vent filter 208 (FIGS. 10B and 13) starts to vent the compressed air from liquid path 214 (FIG. 12) of the transfer device to the atmosphere. This allows the pressure in the expansion chamber 194 (FIGS. 10B and 13) to decrease. As the pressure in the expansion chamber decreases, the compression spring 346 (FIGS. 14B and 23) begins to expand or extend and, with reference to FIG. 10B, the sealing ring 344 of the pressure relief piston assembly moves downwards within the venting bore 322 of the vent housing 320. A venting notch, indicated at 382 in FIGS. 10B and 20, is formed in the vent housing 320. When the sealing ring 344 drops below the notch, the compressed air from within the expansion chamber 194 bypasses the sealing ring and enters the venting bore 322. This causes further movement of the sealing ring 344 downwards into the expansion chamber so that the remaining pressurized air within the expansion chamber quickly vents through the venting bore 322 and out through a venting port 384 (FIG. 4) formed in injection device support surface 227 to atmosphere in a final venting stage.

After the final venting stage, the pressure within the expansion chamber 194 (FIG. 10B) is at atmospheric so that there is no longer pressure pushing up on the bottom of the sealing ring 344 of the pressure relieve piston assembly. As a result, the compression spring 346 (FIGS. 14B and 23) is free to further expand and the piston head drops downwards with respect to the pivot plate 308. As this occurs, the stop 342 (FIGS. 23 and 25) slides down and off of the pivot plate stop surface (358 of FIGS. 23-25). Piston arms 336*a* and 336*b* then drop down through opposing slots 364*a* and 364*b* of FIGS. 24 and 25 and clear of the pivot plate 308 as the compression spring further expands. With the piston arms 336*a* and 336*b* clear of the pivot plate 308, the pivot plate further turns in the direction of arrow 374 of FIG. 25 or arrow 312 of FIG. 17 (counterclockwise) due to the urging of torsion spring 354 (FIGS. 14A and 18). As a result, with reference to FIG. 17, the pivot plate 308 pivots off of the latch hook (305 of FIG. 16) of the retainer strap 300 so that the strap is released. The retainer strap 300 then pivots via the pins 303 (FIG. 16) on the opposite end so that the injection device may be removed from the transfer device for use by a patient.

Although the present subject matter is described herein with reference to specific structures, methods and examples, this is for purposes of illustration only, and it is understood that the present subject matter is applicable to a large range of devices and systems that may differ in particular configuration and appearance while still employing this subject matter.

What is claimed is:

1. A transfer device for transferring a medical fluid from a vial to a medical fluid injection device comprising:

a) a vial elevator configured to receive a vial containing a medical fluid;

b) a vial elevator shaft within which the vial elevator moves between an extended position and a retracted position;

c) a vial spike positioned within the vial elevator shaft so that the vial spike is positioned within the vial when the vial elevator is in the retracted position;

d) an expansion chamber in fluid communication with the vial spike via a gas passage;

e) an injection device port in fluid communication with the vial spike via a liquid passage;

f) a pressurized gas cartridge positioned with the expansion chamber;

g) a puncture tip;

h) a trigger spring having a hammer, said trigger spring configured to be deflected and released as the vial elevator moves from the extended position into the retracted position; and i) a flexible wall portion positioned adjacent to the pressurized gas cartridge or the puncture tip and configured to be engaged by the hammer of the trigger spring upon release of the trigger spring after deflection so that the flexible wall portion causes the puncture tip to puncture the pressurized gas cartridge so as to pressurize the expansion chamber.

2. The transfer device of claim 1 further comprising a passage plate and wherein the gas and liquid passages are formed in the passage plate.

3. The transfer device of claim 2 wherein the gas and liquid passages are cut into the passage plate.

4. The transfer device of claim 2 wherein the gas and liquid passages are molded into the passage plate.

5. The transfer device of claim 1 further comprising a vent filter positioned in circuit with the liquid passage.

6. The transfer device of claim 1 wherein the vial elevator shaft includes shaft cam ramps and the vial elevator includes a plurality of locking arms that are moved radially inwards by the shaft cam ramps as the vial elevator is moved towards the retracted position, each of said locking arms including a locking shoulder configured to engage a vial inserted in the vial elevator when the vial elevator is in the retracted position.

7. The transfer device of claim 6 where in the vial elevator includes a plurality of radially extending locking tabs, each of said locking tabs including a locking post, and each of said locking arms including a locking claw, said locking claws engaging the locking tabs to restrict movement of the vial elevator towards the retracted position when the locking posts are not engaged by a vial positioned in the vial elevator, and said locking tabs being moved into a position where they are not engaged by the locking claws as the vial elevator moves towards the retracted position when the locking posts are engaged by a vial positioned in the vial elevator.

8. The transfer device of claim 7 wherein the vial elevator includes a vial spike opening that receives the vial spike when the vial elevator is in the retracted position, said vial spike configured so that the vial spike does not pass through the vial spike opening when the vial elevator locking claws engage the locking tabs.

9. The transfer device of any of the preceding claims wherein the vial elevator includes a camming hook and further comprising a cam ring rotatably positioned around the vial elevator, said cam ring including a camming surface configured to be traversed by the camming hook as the vial elevator moves from the extended position to the retracted position whereby the cam ring rotates and said cam ring configured to deflect and release the trigger spring as the cam ring rotates.

10. The transfer device of claim 9 wherein the cam ring includes a link hook and further comprising a link attached to the link hook and the trigger spring, said link configured to deflect and release the trigger spring as the cam ring rotates.

11. The transfer device of either one of claims 9 and 10 wherein the vial elevator includes a spline upon which the camming hook is positioned and wherein the elevator shaft includes a slot within which the spline travels as the vial elevator moves from the extended position to the retracted position.

12. The transfer device of any of claims 9 through 11 further comprising a venting bore and a piston assembly, said piston assembly including a piston spring and a seal wherein said piston spring is configured to urge the seal towards a position where a flow of air is permitted through the venting bore when a pressure within the expansion chamber drops below a first predetermined level.

13. The transfer device of claim 12 further comprising a retainer strap configured to secure an injection device to the transfer device and a pivot plate, wherein the pivot plate is pivotally mounted to the transfer device so as to pivot between a latching position wherein the pivot plate engages the retainer strap and a release position wherein the retainer strap is released, said pivot plate operatively connected to the piston assembly so that the pivot plate pivots to the release position when a pressure within the expansion chamber drops below a second predetermined level.

14. The transfer device of claim 13 wherein the piston spring is a compression coil spring and further comprising a torsion spring configured to urge the pivot plate towards the release position.

15. The transfer device of claim 1 wherein the vial spike includes a cannula in fluid communication with the liquid passage and a gas tube positioned within the cannula, wherein the gas tube is in fluid communication with the gas passage.

* * * * *